(12) United States Patent
Dunki-Jacobs et al.

(10) Patent No.: US 11,944,503 B2
(45) Date of Patent: Apr. 2, 2024

(54) SYSTEMS AND METHODS FOR PREVENTING TISSUE MIGRATION IN SURGICAL STAPLERS

(71) Applicant: Standard Bariatrics, Inc., Cincinnati, OH (US)

(72) Inventors: Adam R. Dunki-Jacobs, Cincinnati, OH (US); Mark S. Ortiz, Milford, OH (US); Jonathan R. Thompson, Cincinnati, OH (US); Richard P. Nuchols, Williamsburg, OH (US); Caleb J. Hayward, Goshen, OH (US); Robert T. Means, III, Cincinnati, OH (US); Saylan J. Lukas, Cincinnati, OH (US)

(73) Assignee: Standard Bariatrics, Inc., Cincinnati, OH (US)

( * ) Notice: Subject to any disclaimer, the term of this patent is extended or adjusted under 35 U.S.C. 154(b) by 0 days.

(21) Appl. No.: 18/085,687

(22) Filed: Dec. 21, 2022

(65) Prior Publication Data
US 2023/0132795 A1    May 4, 2023

Related U.S. Application Data

(63) Continuation of application No. 17/857,515, filed on Jul. 5, 2022, which is a continuation of application
(Continued)

(51) Int. Cl.
*A61B 17/064* (2006.01)
*A61B 17/072* (2006.01)
*A61B 90/00* (2016.01)

(52) U.S. Cl.
CPC ........ *A61B 90/03* (2016.02); *A61B 17/07207* (2013.01); *A61B 2017/07257* (2013.01);
(Continued)

(58) Field of Classification Search
CPC .......................... A61B 17/07207; A61B 90/03
See application file for complete search history.

(56) References Cited

U.S. PATENT DOCUMENTS

| 4,676,774 A | 6/1987 | Semm |
| 8,852,218 B2 * | 10/2014 | Hughett, Sr. .... A61B 17/12022 606/157 |

(Continued)

FOREIGN PATENT DOCUMENTS

EP    3075327 A2 *  10/2016    ........... A61B 17/068

OTHER PUBLICATIONS

National Instruments Corp.: Motion Control: FlexMotion-6C Hardware User Manual; Jul. 1999; 86 pages; United States of America.
(Continued)

*Primary Examiner* — Eyamindae C Jallow

(57) ABSTRACT

A surgical instrument including a system for stopping a beam of the surgical instrument from impacting a distal pin when reversing a knife is disclosed. A knife assembly of the surgical instrument comprises the knife, the beam, and a firing nut. A firing lead screw can drive the firing nut distally and proximally. A firing screw compression spring extends along the firing lead screw and applies a load proximally on the firing nut when the firing nut is driven toward a distal end of the firing lead screw.

18 Claims, 19 Drawing Sheets

Related U.S. Application Data

No. 17/700,599, filed on Mar. 22, 2022, now Pat. No. 11,452,574.

(60) Provisional application No. 63/164,837, filed on Mar. 23, 2021.

(52) U.S. Cl.
CPC ............... *A61B 2017/07271* (2013.01); *A61B 2017/07285* (2013.01); *A61B 2090/036* (2016.02)

(56) References Cited

U.S. PATENT DOCUMENTS

| | | | | |
|---|---|---|---|---|
| 10,542,986 | B2* | 1/2020 | Thompson | A61B 17/3468 |
| 2006/0036267 | A1 | 2/2006 | Saadat et al. | |
| 2011/0087259 | A1* | 4/2011 | Marczyk | A61B 17/072 |
| | | | | 606/170 |
| 2011/0114702 | A1* | 5/2011 | Farascioni | A61B 17/068 |
| | | | | 227/176.1 |
| 2011/0163150 | A1* | 7/2011 | Farascioni | A61B 17/068 |
| | | | | 227/181.1 |
| 2011/0264137 | A1* | 10/2011 | Farascioni | A61B 17/07207 |
| | | | | 606/205 |
| 2012/0080473 | A1* | 4/2012 | Farascioni | A61B 17/068 |
| | | | | 227/175.1 |
| 2012/0248170 | A1* | 10/2012 | Marczyk | A61B 90/03 |
| | | | | 227/175.1 |
| 2012/0277525 | A1 | 11/2012 | O'Dea | |
| 2014/0081176 | A1 | 3/2014 | Hassan et al. | |
| 2014/0148731 | A1 | 5/2014 | Radl et al. | |
| 2015/0320421 | A1* | 11/2015 | Marczyk | A61B 17/07207 |
| | | | | 227/176.1 |
| 2016/0262750 | A1* | 9/2016 | Hausen | A61B 17/07207 |
| 2016/0262752 | A1* | 9/2016 | Marczyk | A61B 90/03 |
| 2016/0324527 | A1 | 11/2016 | Thompson et al. | |
| 2018/0311009 | A1* | 11/2018 | Marczyk | A61B 90/03 |
| 2019/0046189 | A1* | 2/2019 | Dunki-Jacobs | A61B 17/07207 |

OTHER PUBLICATIONS

Chekan, E. et al.; Surgical stapling device-tissue interactions: what surgeons need to know to improve patient outcomes; Dovepress; Medical Devices: Evidence and Research 2014(7):305-18; Sep. 12, 2014; URL: https://www.ncbi.nlm.nih.gov/pmc/articles/PMC4168870/.

International Search Report and Written Opinion of the International Searching Authority received in International Patent App. No. PCT/US2020/058960; dated Feb. 2, 2021; 16 pages.

* cited by examiner

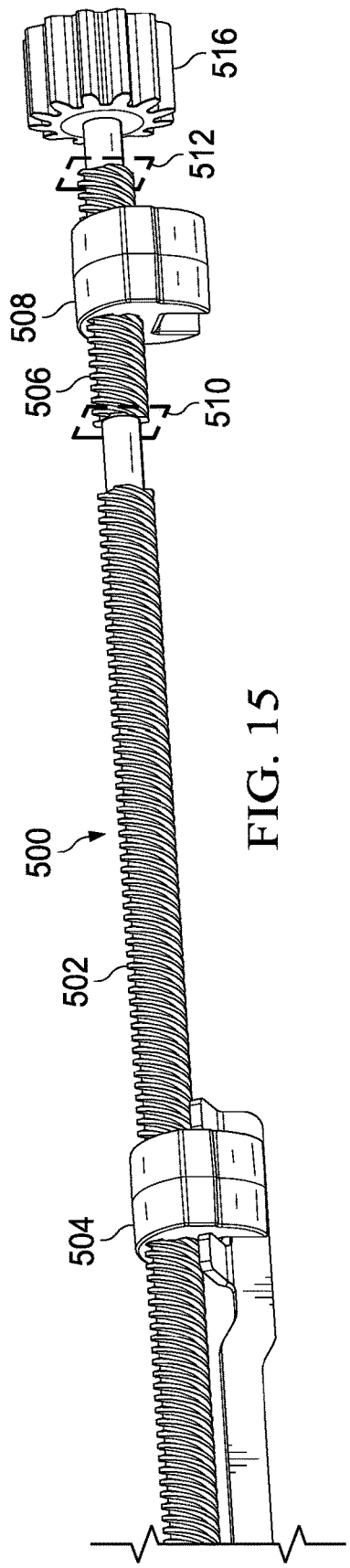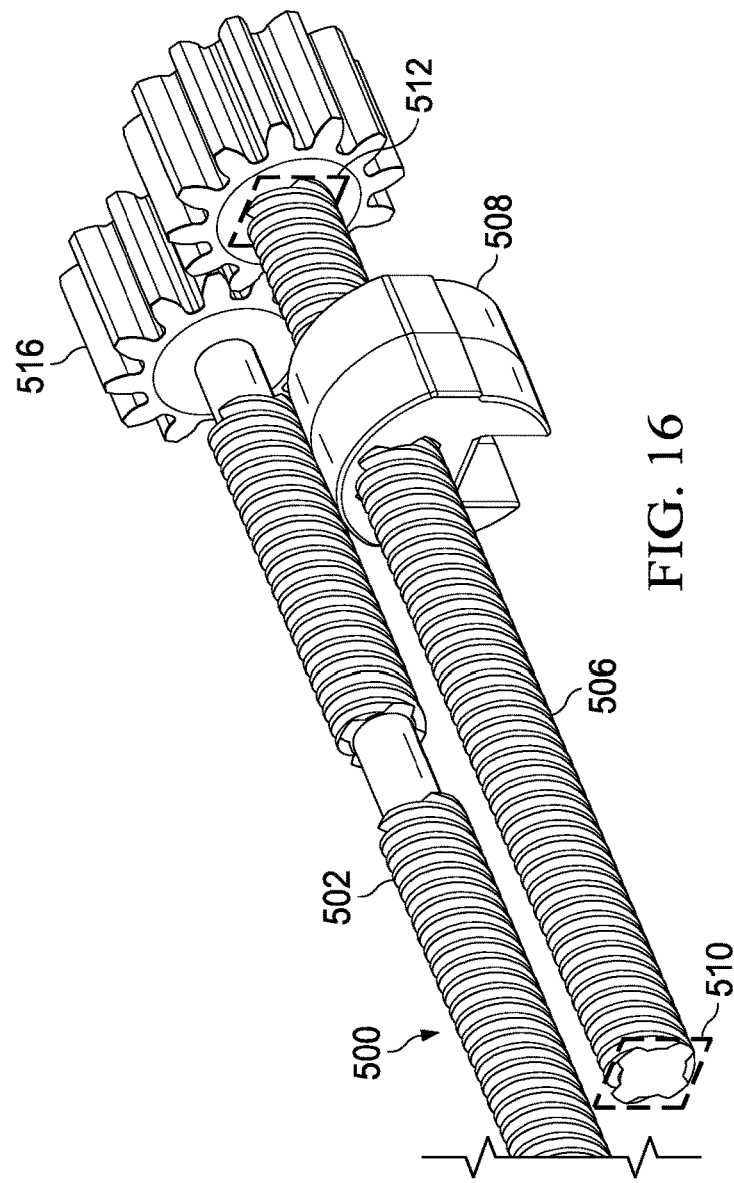

SYSTEMS AND METHODS FOR PREVENTING TISSUE MIGRATION IN SURGICAL STAPLERS

CROSS REFERENCE TO RELATED APPLICATIONS

This application is a continuation of U.S. patent application Ser. No. 17/857,515, filed on Jul. 5, 2022, which is a continuation of U.S. patent application Ser. No. 17/700,599, filed on Mar. 22, 2022, which claims the priority benefit of U.S. Provisional Patent Application No. 63/164,837, filed Mar. 23, 2021, which are hereby incorporated herein by reference in their entirety.

BACKGROUND

The disclosed inventive subject matter relates in general to medical devices and surgical instruments and more specifically to systems, devices, and methods associated with surgical staplers used for bariatric surgery performed using laparoscopic techniques.

Vertical sleeve gastrectomy is a commonly performed type of bariatric surgery in which a surgical stapling instrument is used to remove a portion of the stomach and staple the remaining portion of the stomach closed. Stapling instruments used for this procedure typically include an upper jaw that is connected to a lower jaw at one end thereof using a hinge. Such devices usually include a tissue stop at or near the hinge to prevent the undesirable migration of tissue into the hinged region of the stapler during use. More recently developed stapling instruments such as the TITAN® SGS23R (Standard Bariatrics) and similar instruments include an upper jaw that is connected to a lower jaw at two locations, namely at both ends of the jaws. Staplers having this design include a distal tissue stop and a proximal tissue stop formed on the lower jaws thereof. However, when in the stapler is in an open position, an area exists between the jaws adjacent to the proximal tissue stop into which tissue may migrate during use of the instrument. This migration may continue until a certain degree of closure is reached, at which point the upper jaw engages the proximal tissue stop of the lower jaw to create a tissue barrier. If a surgeon inadvertently closes the stapler on stomach tissue outside the portion of the instrument that ejects staples, transection of tissue without mechanical fastening thereof with staples may result. If this situation is not recognized by the surgeon during the medical procedure, post-operative complications such as leaks may occur. Because this is an undesirable outcome, an additional barrier or other means of preventing tissue migration in surgical stapling instruments would be beneficial.

SUMMARY

The following provides a summary of certain example implementations of the disclosed inventive subject matter. This summary is not an extensive overview and is not intended to identify key or critical aspects or elements of the disclosed inventive subject matter or to delineate its scope. However, it is to be understood that the use of indefinite articles in the language used to describe and claim the disclosed inventive subject matter is not intended in any way to limit the described inventive subject matter. Rather the use of "a" or "an" should be interpreted to mean "at least one" or "one or more".

One implementation of the disclosed technology provides a system for preventing unwanted tissue migration in surgical staplers, comprising a surgical stapler having an end effector for dispensing surgical staples, wherein the end effector includes an upper jaw the upper jaw including a proximal end and a distal end; a lower jaw, the lower jaw including a proximal end and a distal end, wherein the distal end of the upper jaw is connected to the distal end of the lower jaw, and wherein the proximal end of the upper jaw is connected to the proximal end of the lower jaw; a first tissue stop formed on the distal end of the lower jaw; a second tissue stop formed on the proximal end of the of the lower jaw, wherein the second tissue stop and the proximal end of the upper jaw define a no tissue zone when the surgical stapler is in an open position; and a tissue cutting device disposed within the lower jaw for resecting tissue; and a warning, blocking, impeding, or barrier forming device for preventing the unwanted migration of tissue into the no tissue zone during surgical procedures such that resection of unstapled tissue is prevented.

The warning, blocking, impeding, or barrier forming device may include at least one warning label placed on the stapler for alerting a user of the stapler to the no tissue zone. The warning, blocking, impeding, or barrier forming device may include a flexible sheath, wherein the flexible cape is placed partially or completely around the proximal ends of the upper and lower jaws while permitting the opening and closing thereof. The warning, blocking, impeding, or barrier forming device may include a rigid shield, wherein the rigid shield is formed on or attached to the proximal end of the upper jaw. The warning, blocking, impeding, or barrier forming device may include a flexible band attached to the upper jaw and to the lower jaw and extending therebetween, and wherein at least a portion of the flexible band is located in front of the second tissue stop. The warning, blocking, impeding, or barrier forming device may include a post extending between the upper jaw and the lower jaw at the front end of the second tissue stop, wherein the post either rotates or telescopes when the jaws open and close. The warning, blocking, impeding, or barrier forming device may include a curved or hinged closure link extending between the proximal ends of the upper jaw and the lower jaw. The warning, blocking, impeding, or barrier forming device may include a sacrificial band of compliant material, block of compliant material, or compliant balloon positioned between the proximal ends of the upper jaw and the lower jaw. The warning, blocking, impeding, or barrier forming device may include a non-sacrificial block of rigid material or piece of expandable material positioned between the proximal ends of the upper jaw and the lower jaw and adapted to permit the tissue cutting device to pass therethrough.

Another implementation of the disclosed technology provides a system for preventing unwanted tissue migration in surgical staplers, comprising a surgical stapler having an end effector for dispensing surgical staples, wherein the end effector includes an upper jaw the upper jaw including a proximal end and a distal end; a lower jaw, the lower jaw including a proximal end and a distal end, wherein the distal end of the upper jaw is connected to the distal end of the lower jaw, and wherein the proximal end of the upper jaw is connected to the proximal end of the lower jaw; a first tissue stop formed on the distal end of the lower jaw; a second tissue stop formed on the proximal end of the of the lower jaw, wherein the second tissue stop and the proximal end of the upper jaw define a no tissue zone when the surgical stapler is in an open position; and a tissue cutting device disposed within the lower jaw for resecting tissue; and a mechanism for preventing the unwanted migration of tissue into the no tissue zone during surgical procedures such that resection of unstapled tissue is prevented.

The mechanism may disengage the tissue cutting device before it reaches the no tissue zone. The mechanism may stop the tissue cutting device before it reaches the no tissue zone and reverses its direction of travel toward the distal end of the lower jaw. The mechanism may use software or software and sensors associated with the operation of the stapler for detecting the presence of tissue within the no tissue zone and taking corrective action. The system may also include audible, visual, or tactile indicators, or various combinations thereof, that are triggered by the software or software and sensors when the presence of tissue is detected within the no tissue zone.

Another implementation of the disclosed technology provides a method for preventing unwanted tissue migration in a surgical stapler having an end effector for dispensing surgical staples, wherein the end effector includes an upper jaw having proximal end and a distal end; a lower jaw having a proximal end and a distal end, wherein the distal end of the upper jaw is connected to the distal end of the lower jaw, and wherein the proximal end of the upper jaw is connected to the proximal end of the lower jaw; a first tissue stop formed on the distal end of the lower jaw; a second tissue stop formed on the proximal end of the of the lower jaw, wherein the second tissue stop and the proximal end of the upper jaw define a no tissue zone when the surgical stapler is in an open position; and a tissue cutting device disposed within the lower jaw for resecting tissue, the method comprising providing a warning, blocking, impeding, or barrier forming device for preventing the unwanted migration of tissue into the no tissue zone during surgical procedures such that resection of unstapled tissue is prevented; or providing a mechanism for preventing the unwanted migration of tissue into the no tissue zone during surgical procedures such that resection of unstapled tissue is prevented.

The warning, blocking, impeding, or barrier forming device may include at least one warning label placed on the stapler for alerting a user of the stapler to the no tissue zone. The warning, blocking, impeding, or barrier forming device may include a flexible sheath, wherein the flexible cape is placed partially or completely around the proximal ends of the upper and lower jaws while permitting the opening and closing thereof. The warning, blocking, impeding, or barrier forming device may include a rigid shield, wherein the rigid shield is formed on or attached to the proximal end of the upper jaw. The warning, blocking, impeding, or barrier forming device may include a flexible band attached to the upper jaw and to the lower jaw and extending therebetween, and wherein at least a portion of the flexible band is located in front of the second tissue stop. The warning, blocking, impeding, or barrier forming device may include a post extending between the upper jaw and the lower jaw at the front end of the second tissue stop, wherein the post either rotates or telescopes when the jaws open and close. The warning, blocking, impeding, or barrier forming device may include a curved or hinged closure link extending between the proximal ends of the upper jaw and the lower jaw. The warning, blocking, impeding, or barrier forming device may include a sacrificial band of compliant material, block of compliant material, or compliant balloon positioned between the proximal ends of the upper jaw and the lower jaw. The warning, blocking, impeding, or barrier forming device may include a non-sacrificial block of rigid material or piece of expandable material positioned between the proximal ends of the upper jaw and the lower jaw and adapted to permit the tissue cutting device to pass therethrough. The mechanism may disengage the tissue cutting device before it reaches the no tissue zone. The mechanism may stop the tissue cutting device before it reaches the no tissue zone and reverses its direction of travel toward the distal end of the lower jaw. The mechanism may use software or software and sensors associated with the operation of the stapler for detecting the presence of tissue within the no tissue zone and taking corrective action Audible, visual, or tactile indicators, or various combinations thereof, that are triggered by the software or software and sensors when the presence of tissue is detected within the no tissue zone, may also be provided.

It should be appreciated that all combinations of the foregoing concepts and additional concepts discussed in greater detail below (provided such concepts are not mutually inconsistent) are contemplated as being part of the inventive subject matter disclosed herein and may be implemented to achieve the benefits as described herein. Additional features and aspects of the disclosed system, devices, and methods will become apparent to those of ordinary skill in the art upon reading and understanding the following detailed description of the example implementations. As will be appreciated by the skilled artisan, further implementations are possible without departing from the scope and spirit of what is disclosed herein. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more example implementations of the disclosed inventive subject matter and, together with the general description given above and detailed description given below, serve to explain the principles of the disclosed subject matter, and wherein:

FIG. 15 depicts an implementation that utilizes a reversing knife approach to preventing the transection of tissue without closure thereof with surgical staples through the inclusion of a secondary thread on the primary firing screw;

FIG. 16 depicts an implementation that utilizes a reversing knife approach to preventing the transection of tissue without the closure thereof with surgical staples through the inclusion of a secondary fine thread on an auxiliary firing screw;

DETAILED DESCRIPTION

Figure 1A:
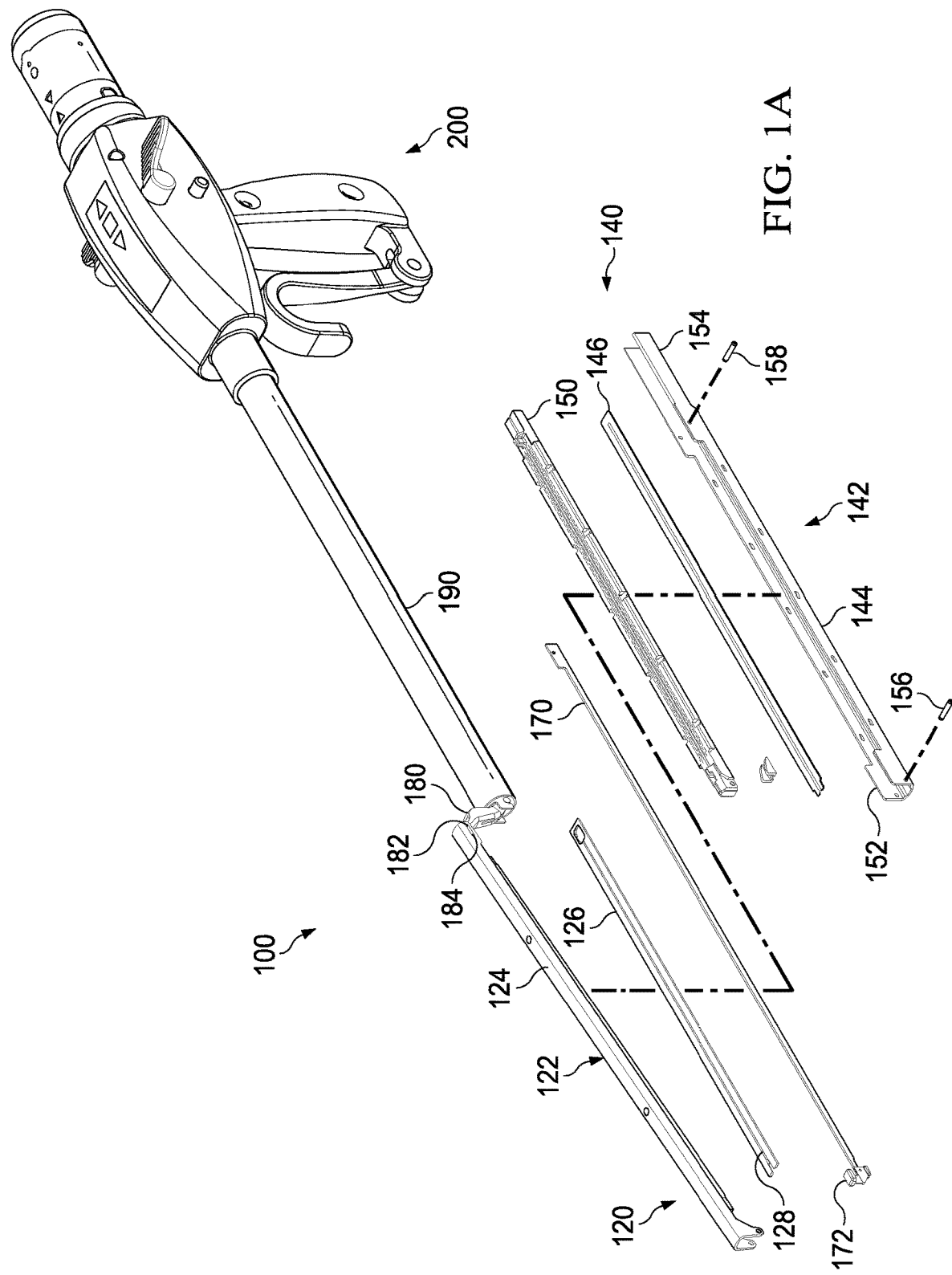
FIGS. 1A and 1B depict, in an exploded view and a perspective view, respectively, an example surgical stapler that is hinged at two locations along the length of the stapler and that includes a no tissue zone into which tissue may unwantedly migrate during surgical procedures such as laparoscopic bariatric surgery.

Example implementations are now described with reference to the Figures. Reference numerals are used throughout the detailed description to refer to the various elements and structures. Although the following detailed description contains many specifics for the purposes of illustration, a person of ordinary skill in the art will appreciate that many variations and alterations to the following details are within the scope of the disclosed inventive subject matter. Accordingly, the following implementations are set forth without any loss of generality to, and without imposing limitations upon, the claimed subject matter.

As previously stated, surgical stapling instruments such as the TITAN® SGS23R (Standard Bariatrics) include an upper jaw that is connected to a lower jaw at two locations, namely at both ends of the jaws. Staplers having this design can include a distal tissue stop and a proximal tissue stop formed on the lower jaws thereof. However, when the stapler is in an open position, an area may exist between the jaws adjacent to the proximal tissue stop into which tissue may migrate during use of the instrument. This migration may be problematic if a surgeon inadvertently closes the stapler on stomach tissue that has migrated outside the portion of the instrument that ejects and secures tissue with staples. In such an area, where tissue has not been stapled, transection of tissue may still progress resulting in a potentially dangerous unstapled portion of the transected tissue. If this situation is not recognized by the surgeon during the medical procedure, post-operative complications such as leaks may occur. Disclosed implementations provide various structural and mechanical systems, devices, and methods for preventing the unwanted migration of tissue when staplers such as the TITAN® SGS23R are used in laparoscopic bariatric surgery.

Staplers compatible with the disclosed technology are described in U.S. Pat. No. 10,687,814, which is incorporated by reference herein in its entirety, for all purposes. Some implementations of the staplers disclosed in U.S. Pat. No. 10,687,814 include end effectors that are attached to a support tube that is attached to a handle that includes an actuator for the instrument. As shown in the Figures of U.S. Pat. No. 10,687,814, example end effectors found on surgical staplers include an upper jaw connected to a lower jaw by a simple hinge at the distal end of the stapler and by a master link or rigid link at the proximal end of the stapler. The upper jaw may include an anvil assembly that further includes an anvil frame, an anvil plate, and an anvil plate channel formed therein. The lower jaw may include a cartridge assembly that further includes a cartridge frame, a cartridge plate with a cartridge plate channel formed therein, and a cartridge for containing surgical staples. The cartridge frame may include a first tissue stop and a second tissue stop as well as first and second cartridge pins. A blade assembly that includes a cutting blade is disposed within the cartridge assembly. The master link may include a master link pin that cooperates with a master link slot.

Figure 1B:
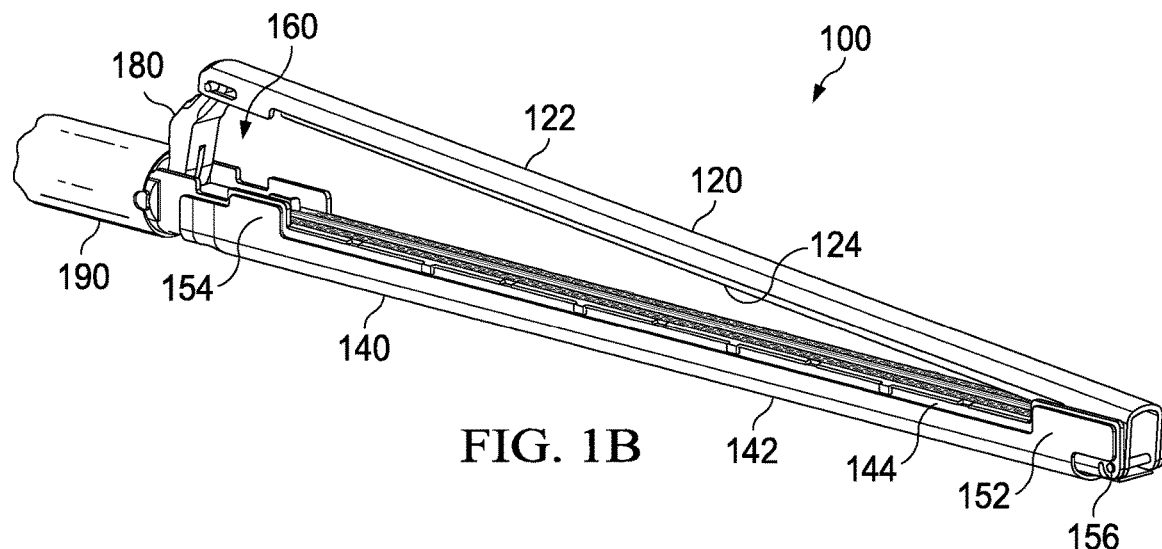

FIGS. 1A-1B depict[[s]] example surgical stapler having end effector 100 (e.g., TITAN® SGS23R), which includes upper jaw 120, lower jaw 140, blade/knife assembly 170, and master link 180. Upper jaw 120 includes anvil assembly 122, which further includes anvil frame 124, anvil plate 126, and anvil plate channel 128. Lower jaw 140 includes cartridge assembly 142, which further includes cartridge frame 144, cartridge plate 146, cartridge 150, distal tissue stop 152, proximal tissue stop 154, distal cartridge pin 156, and proximal cartridge pin 158. Distal cartridge pin 156 connects upper jaw 120 and lower jaw 140 in a hinged manner at the distal end of end effector 100. Blade/knife assembly 170, which includes I-beam or I-shaped knife 172 (see also FIG. 9) is disposed within lower jaw 140. Master link 180 connects upper jaw 120 and lower jaw 140 at the proximal end of end effector 100 in a hinged manner using master pin 182, which is positioned in a sliding manner within master link slot 184. End effector 100 is attached to elongated support tube 190, which is connected to handle 200 (see also FIGS. 5 and 6). Handle 200 includes various mechanical aspects that actuate end effector 100 and knife 172. A region of concern or "no tissue zone" 160 can be any area or space into which tissue may unwantedly migrate during surgical procedures such as laparoscopic bariatric surgery. No tissue zone 160 may be located at the proximal end of the end effector, for example, but may be any area where tissue migration is problematic.

Figure 2:
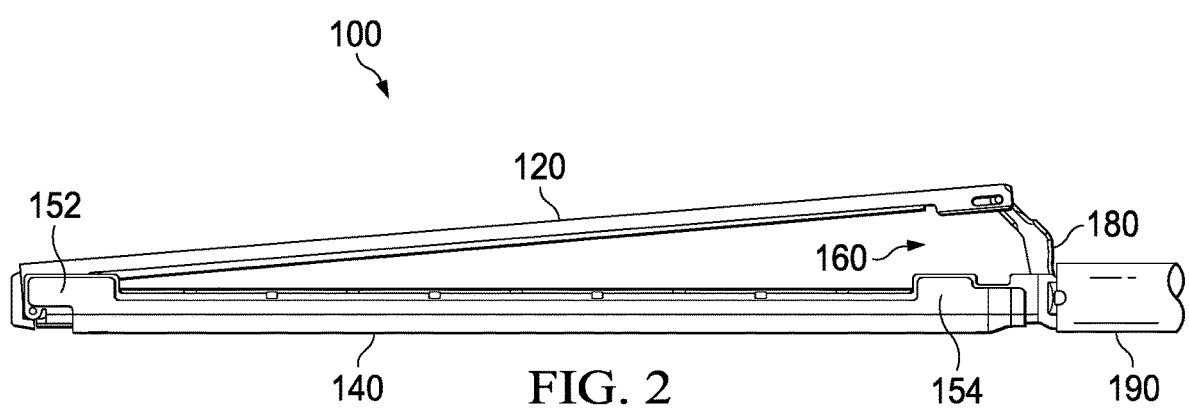
FIG. 2 depicts the surgical stapler of FIG. 1A, wherein a physical label has been placed on the lower jaw of the stapler indicating that "no tissue" is to be situated within the labeled region.

FIG. 2 depicts an example labeling solution to the tissue migration concern. FIG. 2 depicts the surgical stapler of FIG. 1B, wherein a physical label has been placed on the lower jaw of end effector 100 indicating that "no tissue" is to be situated within the labeled region, which is no tissue zone 160). "No tissue" graphics may also be included on top of anvil assembly 122, on upper jaw 120, on the side of cartridge assembly 142, on lower jaw 140, or on any other surface of end effector 100 to alert the user of the risk. Labeling may be affixed to end effector 100 using adhesive, or by screen printing, laser etching, or the like, and may include additional or alternate phrases, as wells as various fonts, colors, and graphics intended to draw the attention of a user to the no tissue zone.

Figure 3:
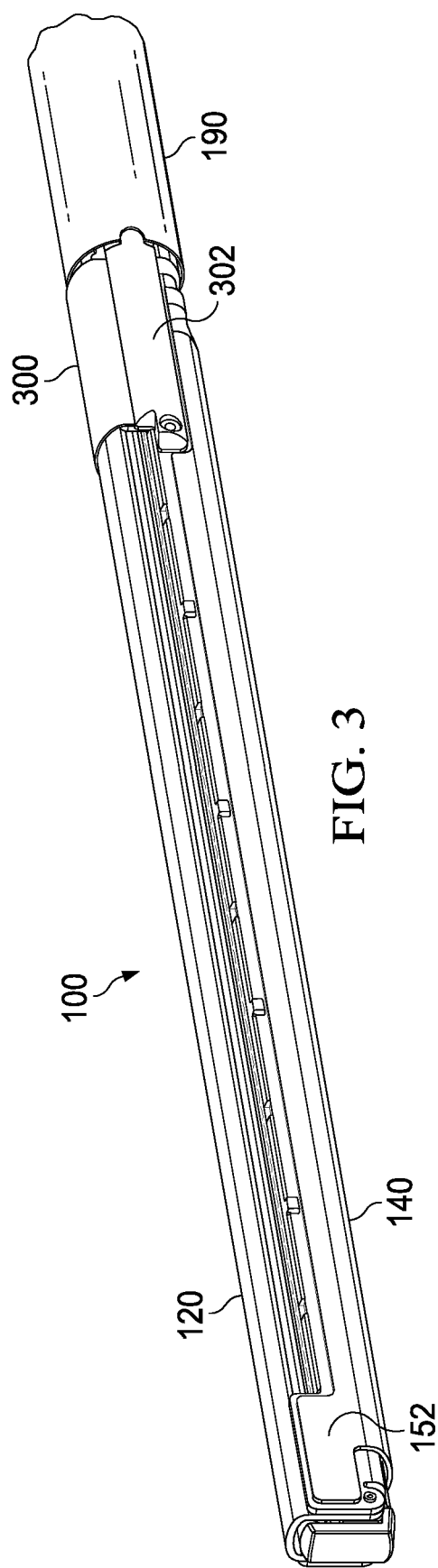
FIG. 3 depicts the stapler of FIG. 1A, wherein the jaws of the stapler are shown in a closed position and wherein a flexible tissue-blocking sheath has been partially wrapped around the upper and lower jaws of the stapler.
Figure 4:
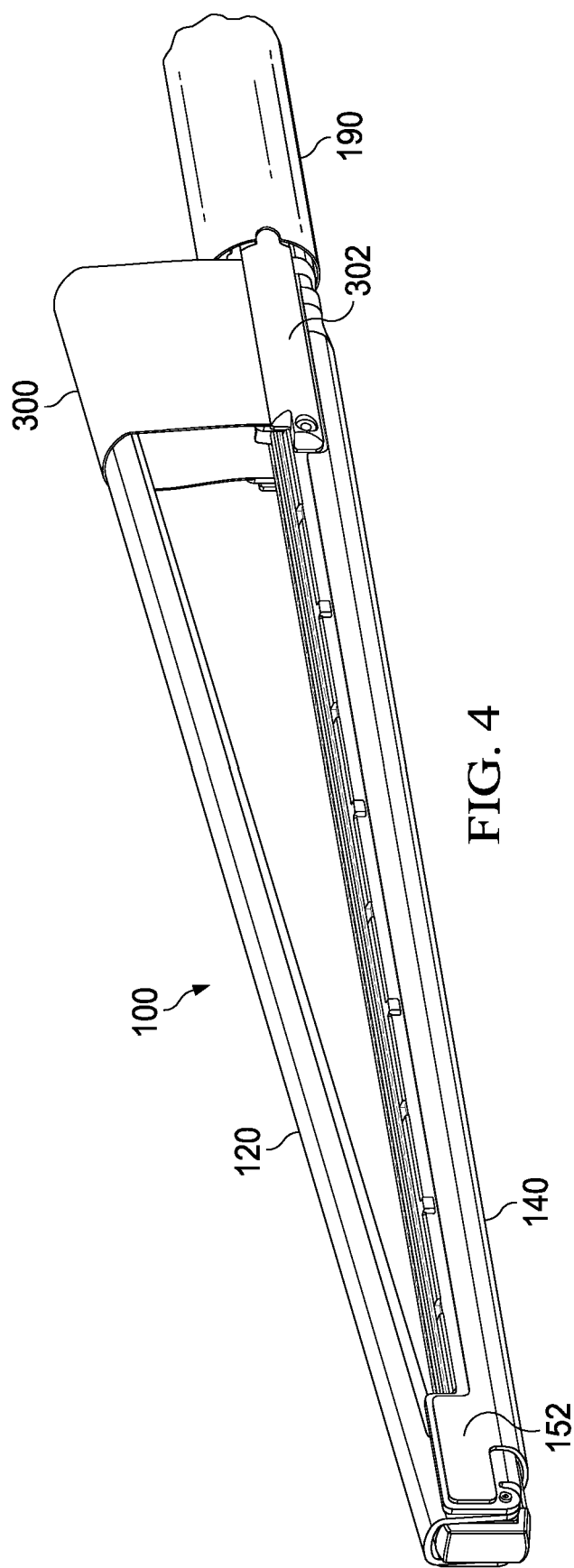
FIG. 4 depicts the stapler of FIG. 1A, wherein the jaws of the stapler are shown in an open position and wherein a flexible tissue-blocking sheath has been partially wrapped around the upper and lower jaws of the stapler.
Figure 5:
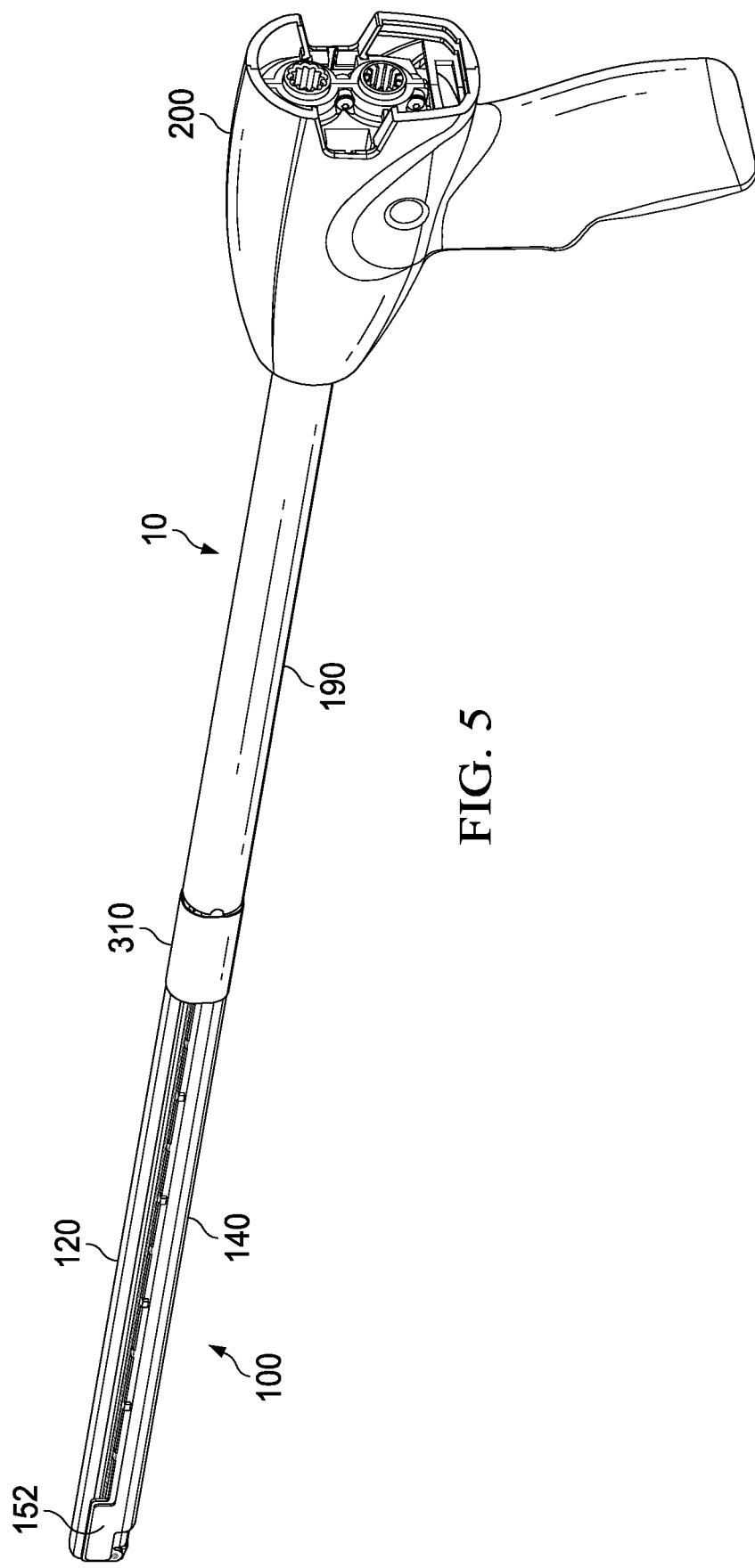
FIG. 5 depicts the stapler of FIG. 1A, wherein the jaws of the stapler are shown in a closed position and wherein a flexible tissue-blocking sleeve has been circumferentially wrapped around the upper and lower jaws of the stapler.
Figure 6:
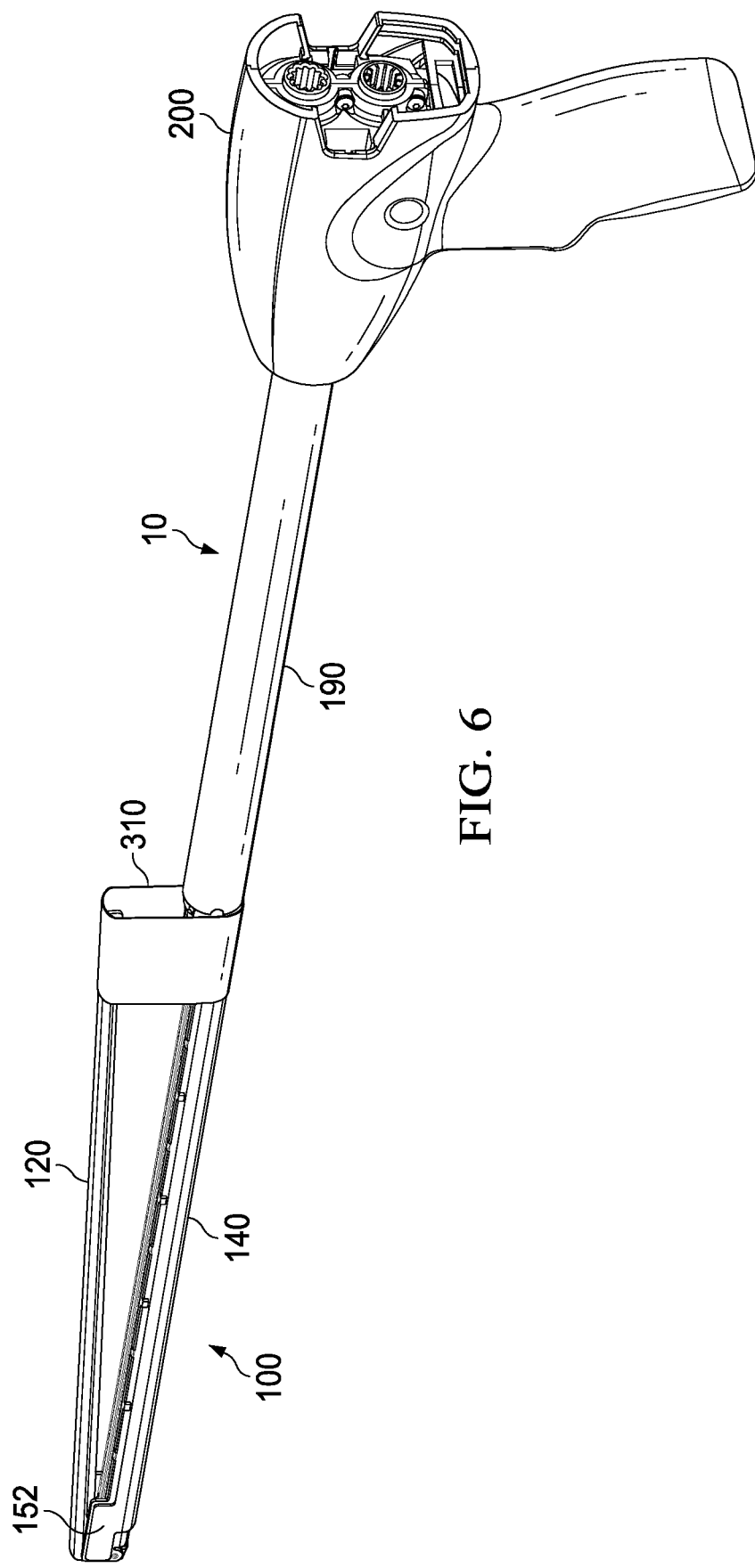
FIG. 6 depicts the stapler of FIG. 1A, wherein the jaws of the stapler are shown in an open position and wherein a flexible tissue-blocking sleeve has been circumferentially wrapped around the upper and lower jaws of the stapler.
Figure 7:
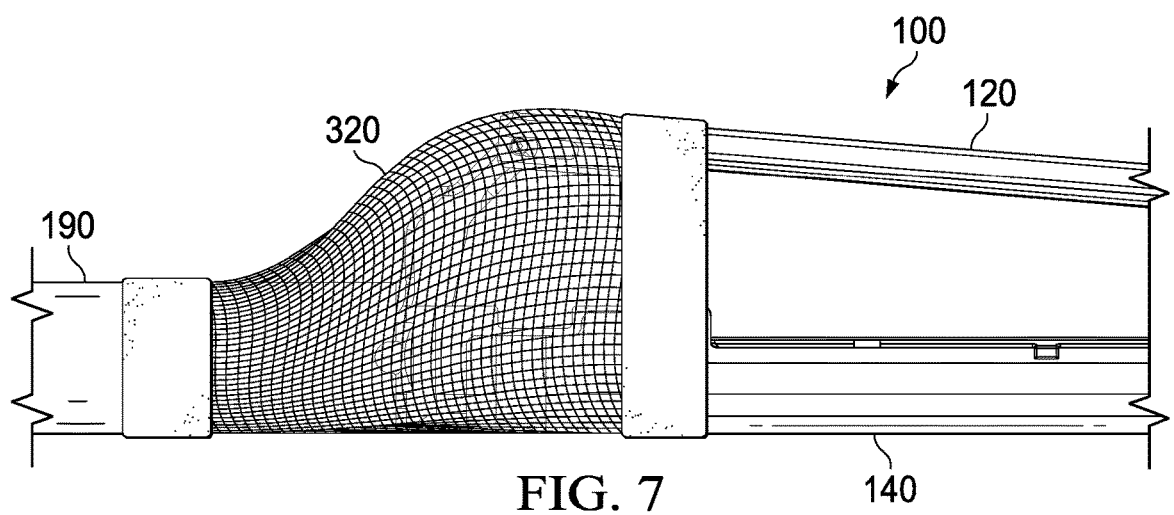
FIG. 7 depicts the stapler of FIG. 1A, wherein the jaws of the stapler are shown in an open position and wherein a flexible, braided, tissue-blocking sleeve has been circumferentially wrapped around the upper and lower jaws of the stapler
Figure 8:
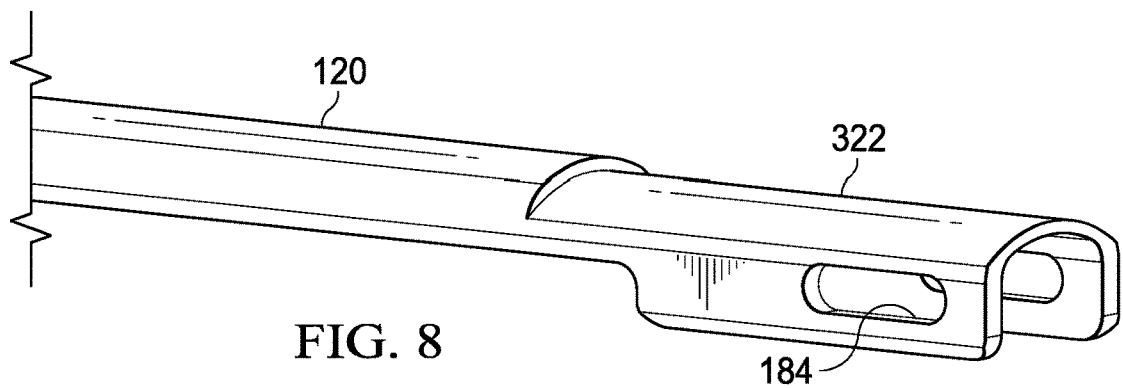
FIG. 8 depicts the upper jaw of the stapler of FIG. 1A, wherein a recessed region has been formed therein for accommodating a flexible sheath or sleeve.

FIGS. 3-8 depict various implementations of a tissue-blocking shield placed around the jaws of end effector 100 for the purpose preventing tissue from migrating into region 160 while still permitting the jaws of end effector 100 to open. FIG. 3 depicts the stapler of FIG. 1B, wherein the jaws of end effector 100 are shown in a closed position and flexible tissue-blocking sheath 300 has been partially wrapped around upper and lower jaws 120 and 140 of end effector 100. FIG. 4 depicts the stapler of FIG. 1B, where the jaws of end effector 100 are shown in an open position and flexible tissue-blocking elastomeric sheath 300 has been partially wrapped around upper and lower jaws 120 and 140 of end effector 100. Sheath lock 302 is included in this implementation for locking cape 300 on end effector 100. Sheath lock 302 may be an overmolded plastic component located on either side of lower jaw 140. Sheath lock 302 may be affixed to lower jaw 140 with a screw or other positive fixation device such as a rivet, pin, orbital rivet, or heat stake. The proximal end of sheath lock 302 is affixed to lower jaw 140 by engaging an interlocking feature in support tube 190. Sheath lock 302 may incorporate a jaw lock component or may engage with a jaw lock to constrain the sheath lock FIG. 5 depicts the end effector of FIG. 1B, where the jaws of end effector 100 are shown in a closed position and elastomeric tissue-blocking sleeve 310 has been circumferentially wrapped around upper and lower jaws 120 and 140 of end effector 100. FIG. 6 depicts the end effector of FIG. 1B, where the jaws of end effector 100 are shown in an open position and elastomeric tissue-blocking sleeve 310 has been circumferentially wrapped around upper and lower jaws 120 and 140 of end effector 100. FIG. 7 depicts the end effector of FIG. 1B, wherein the jaws of end effector 100 are shown in an open position and flexible, braided mesh barrier 320 has been circumferentially wrapped around upper and lower jaws 120 and 140 of end effector 100. FIG. 8 depicts upper jaw 120 of the end effector of FIG. 1B, wherein recessed region 322 has been formed therein for accommodating a flexible cape or sleeve.

The sheath and sleeve described above may be made from a variety of elastic materials including silicone, urethane, or the like, or may be geometrically flexible such as the braided implementation of FIG. 7. The implementation shown in FIG. 7 may include bands placed on both ends of the sleeve to prevent the sleeve from fraying. Alternately, both ends of the sleeve may be overmolded with an elastomeric material to prevent the sleeve from fraying. The sheath and sleeve may be lubricated to minimize drag force when inserting the stapling instrument into a trocar. Lubrication may be achieved by altering the surface finish of the sheath, adding a lubricant to the sheath such as a silicone grease, polytetrafluoroethylene (PTFE) solids or the like, or by doping the sheath material with a lubricant. Adding a stainless steel or plastic spine (not shown) to the top of the sheath may also reduce drag force. The spine may be over-molded to the sheath or rigidly attached to anvil frame 124 by the use of screws or snaps, or by welding, gluing, or other process. Sheath lock 302 member fixes sheath 300 to end effector 100 and may be made of a metal such as stainless steel, or a plastic such as nylon, and may be attached to cartridge frame 144 by a screws, snaps, or other devices. Sheath 300 and sheath lock 302 may be separate components or a single component installed on end effector 100 by over-molding sheath 300 to sheath lock 302. Sheath lock 302 may incorporate a jaw lock component or may engage with a jaw lock to constrain the sheath lock. The previously described no tissue zone labeling may be included on some or all variants of sheath 300.

Figure 9:
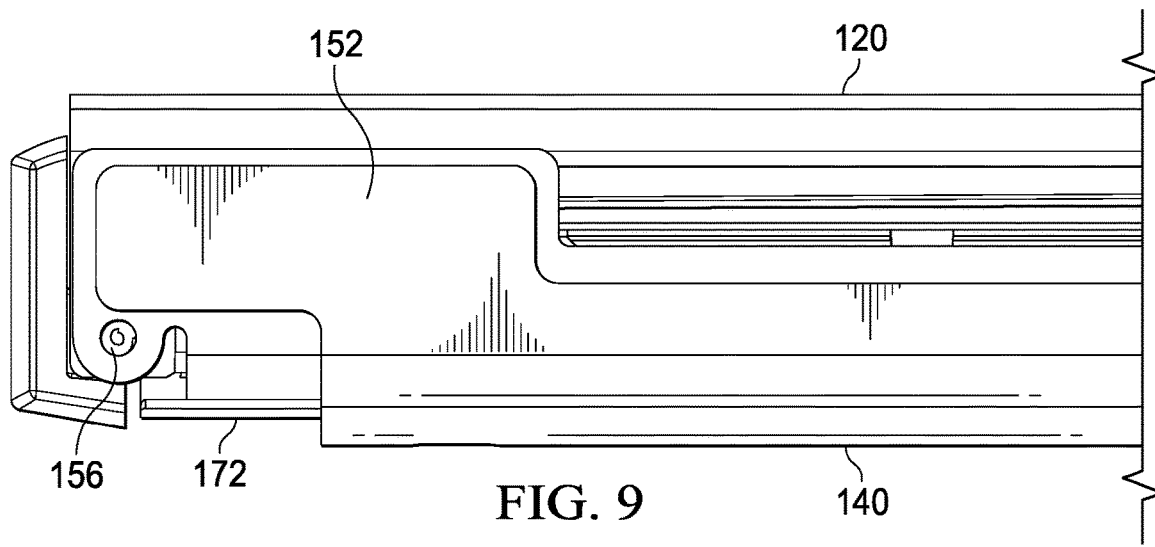
FIG. 9 depicts the stapler of FIG. 1A in a closed position, wherein the tissue cutting knife, also referred to as an I-beam or I-shaped blade, is visible near the distal pin.

FIG. 9 depicts end effector 100 in a closed position where tissue cutting knife 172, also referred to as an I-beam or I-shaped blade, is visible near distal pin 156. Regarding FIG. 9, one implementation of the disclosed technology provides a reversing knife solution to the previously discussed tissue migration concern. This approach eliminates the problem of transecting unstapled tissue by stopping knife 172 before it reaches the no tissue zone at the proximal end of the end effector 100. After transecting only stapled portions of tissue, the knife 172 can be distally to its starting position, tangent to distal pin 156, as shown in FIG. 9. Using this method, knife 172 will not cut tissue without also firing staples along the cut line.

The solution reversing the knife 172, as described above, may be accomplished using software included with commercially available stapling instruments such as, for example, the TITAN® SGS23R "Standard Power Unit" (SPU) software. Once a knife band (see U.S. Pat. No. 10,687,814) activates a limit switch at the proximal limit of firing, such as at the proximal end of the end effector 100, the SPU software can reverse the polarity of the firing motor, to reverse the direction of the knife band. To stop the I-Beam from striking the distal pin 156 when reversing the knife, the SPU can actively monitor the presence of the I-Beam at the distal tip of the end effector 100. A distal limit switch may be attached to end effector 100, stopping the firing motor when the I-Beam has reached its distal position (see FIG. 9). The distal limit switch may be a digital switch that operates in a binary on/off nature depending on whether the I-Beam is at its distal position or not, or an analog sensor that provides a range of values depending on where the I-Beam is located in the firing stroke. If the switch is binary, it may be an off-the-shelf (OTS) single pole single throw (SPST) limit switch that is mounted to a printed circuit board (PCB), a stand-alone OTS limit switch wired back to the SPU by way of a power cable, or a custom limit switch consisting of a movable component that electrically connects (normally open, "NO") or disconnects (normally closed, "NC"), two terminals connected to the SPU. In one implementation, the I-Beam and distal pin 156 cooperate to complete an electric connection and act as a binary switch. If the switch is analog, it may be an OTS analog sensor that is mounted to a PCB or a stand-alone OTS limit switch wired back to the SPU by way of a power cable such as a proximity sensor, ultrasonic sensor, time of light sensor (ToF), laser sensor, light detecting and ranging (LIDAR) sensor, or the like, or a custom analog sensor connected to the SPU. Some implementations include various indicators such as, for example, audible, visual, or tactile indicators, or combinations thereof, that are triggered by the software and sensors when the presence of tissue is detected within no tissue zone 160.

In some implementations, a rotary encoder is included with the firing motor to stop the I-Beam from crashing into distal pin 156 when reversing knife 172, to provide closed-loop feedback of the motor's rotary position. With an encoder, the SPU software monitors the number of motor turns required to activate the proximal firing limit switch and repeats the same number of motor turns to return the knife band to its starting position. Suitable motor encoder technology may be mechanical, optical, or magnetic (hall-effect) to track the rotation of the motor shaft. The SPU may also monitor real-time electrical motor current in amperes to compare to preset current limits when using a device such as the TITAN® SGS23R. The current limits may mitigate damage to the device when in use. The SPU may further monitor the firing motor current when reversing the knife, monitoring for a current spike above a preset threshold to determine when the I-Beam contacts distal pin 156. System software may, for example, only monitor for the current spike at a percentage of the return sequence by means of time or using an encoder as described above. In a similar manner, in an alternate implementation, the SPU monitors the closure motor current for the presence of tissue in the no tissue zone. Tissue in the no tissue zone induces a spike in current on the closure motor within a fixed window of time or closure stroke. Identifying this minimum current spike allows the SPU to detect tissue in the no tissue zone and warn the user of imminent tissue damage and/or prevent the user from firing the device.

Figure 10:
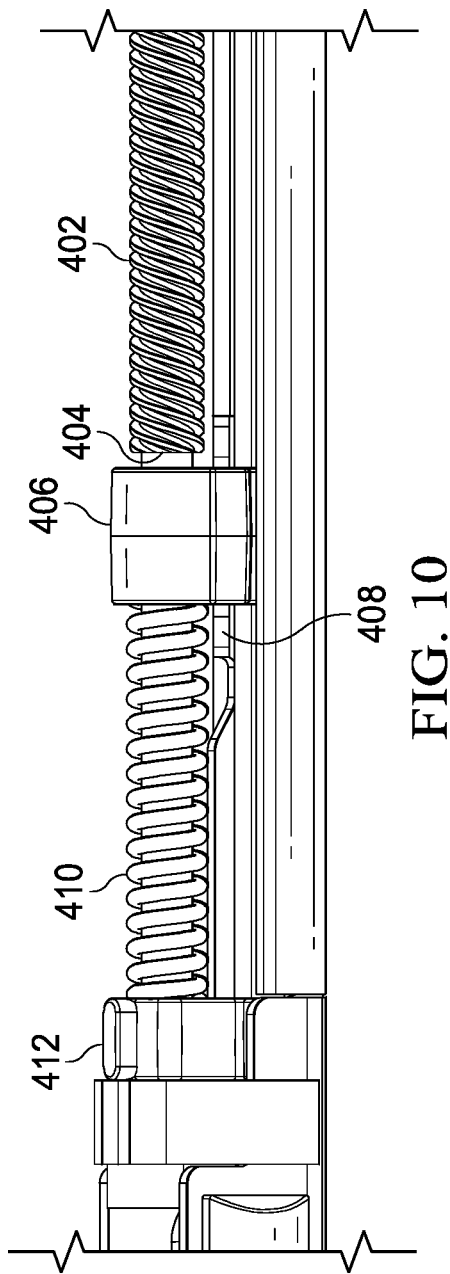
FIG. 10 depicts a mechanical method for stopping the I-Beam from crashing into the distal pin when reversing the knife, wherein the threads on the firing lead screw stop distally, passively limiting the reverse travel of the firing nut.

FIG. 10 depicts another implementation for stopping the I-Beam from striking distal pin 156 when reversing knife 172, wherein the threads on firing lead screw 402 stop distally, passively limiting the reverse travel of firing nut 406. In this implementation, firing nut 406 exhausts the threads on firing lead screw 402 and slips on the threads as firing lead screw 402 continues to turn to drive firing nut 406 distally. Fixed firing screw compression spring 410 applies a load proximally on firing nut 406 and allows firing nut 406 to reengage with firing lead screw 402 when firing lead screw 402 rotates to drive firing nut 406 proximally. Fixed firing lead screw 402 is constrained laterally by firing bushing 412 and the threads of firing lead screw 402, limited by its inner diameter (ID) being less than the major diameter of the threads of firing lead screw 402.

Figure 11:
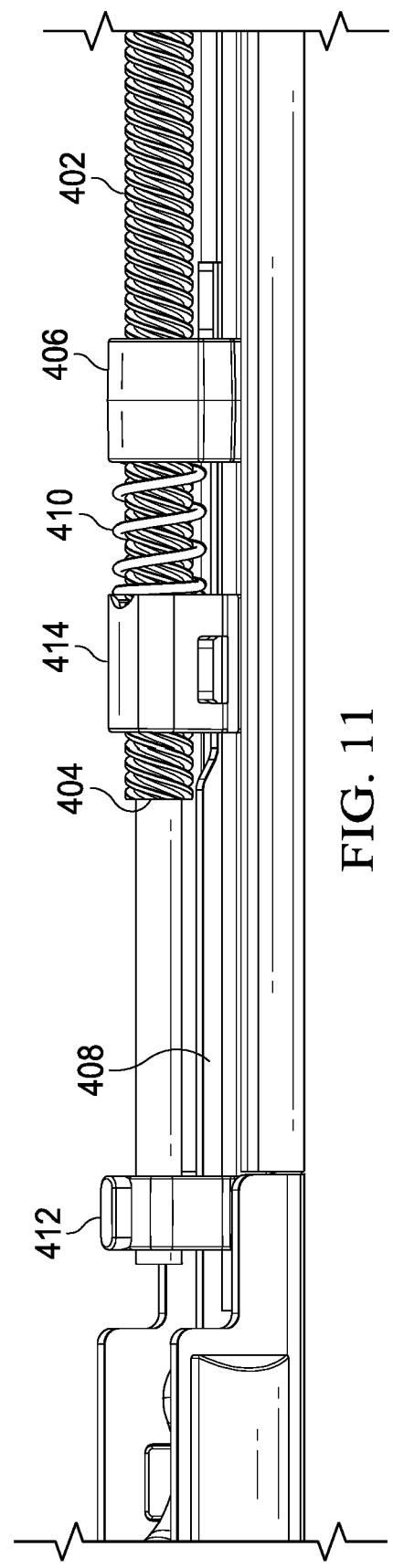
FIG. 11 depicts a mechanical method for stopping the I-Beam from striking the distal pin when reversing the knife, where the threads on the firing lead screw stop distally, passively limiting the reverse travel of the firing nut, but where the firing screw compression spring is mobile rather than fixed.

FIG. 11 depicts another implementation for stopping the I-Beam from crashing into distal pin 156 when reversing knife 172, wherein the threads on firing screw 402 stop distally, passively limiting the reverse travel of firing nut 406, but where firing screw compression spring 410 is mobile rather than fixed. In this implementation, mobile firing screw compression spring 410 is constrained by nut plate 414 and firing nut 406, and spring 410 travels along the threaded and unthreaded portion of firing lead screw 402 as firing nut 406 and nut plate 414 travel. Nut plate 414 is unthreaded, unlike firing nut 406, and slides along the threaded and unthreaded portion of firing lead screw 402 like mobile firing screw compression spring 410. When firing nut 406 exhausts the threads on firing lead screw 402, it will slip on the threads as firing lead screw 402 continues to turn to drive firing nut 406 distally. Unlike the previous implementation, this variant anticipates a crash of the I-Beam and distal pin 156, but mobile firing screw compression spring 410 provides a compliant power transfer from firing nut 406 and knife band 408 when firing nut 406 is driven distally.

Figure 12:
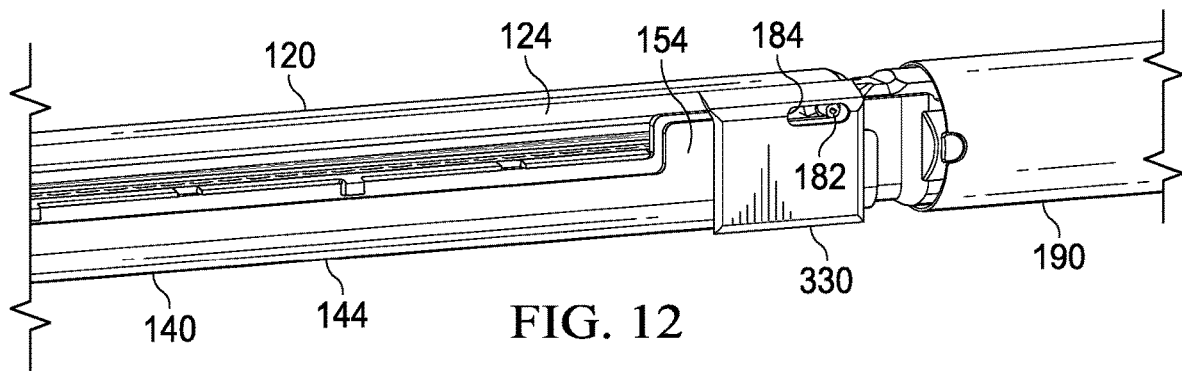
FIG. 12 depicts the stapler of FIG. 1A, where the jaws of the stapler are shown in a closed position and where a tissue-blocking anvil cap has been formed or placed on the upper jaw of the stapler.
Figure 13:
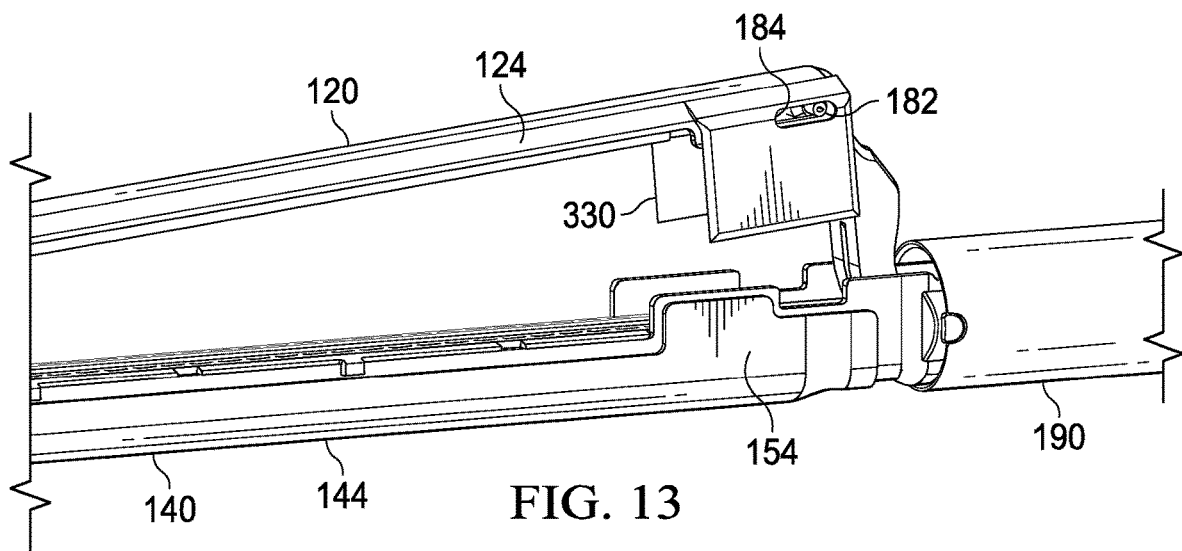
FIG. 13 depicts the stapler of FIG. 1A, where the jaws of the stapler are shown in an open position and wherein a tissue-blocking anvil cap has been formed or placed on the upper jaw of the stapler.

FIG. 12 depicts end effector 100, wherein the jaws of end effector 100 are shown in a closed position and wherein tissue-blocking anvil cap 330 has been formed or placed on upper jaw 120 of end effector 100. FIG. 13 depicts end effector 100, wherein the jaws of end effector 100 are shown in an open position and wherein tissue-blocking anvil cap 330 has been formed or placed on upper jaw 120 of end effector 100. In this implementation, anvil cap 300 may be formed on anvil frame 124 or may be rigidly attached thereto as a separate structure using welding, adhesives, or attachment hardware such as bolts or screws. Anvil cap 330 cooperates with second proximal tissue stop 154 on cartridge frame 144 to create a shield for preventing tissue from entering no tissue zone 160. When upper and lower jaws 120 and 140 are closed, anvil cap 330 may not protrude past the bottom edge of cartridge frame 144. When upper and lower jaws 120 and 140 are open, anvil cap 330 can shield the no tissue zone.

Figure 14:
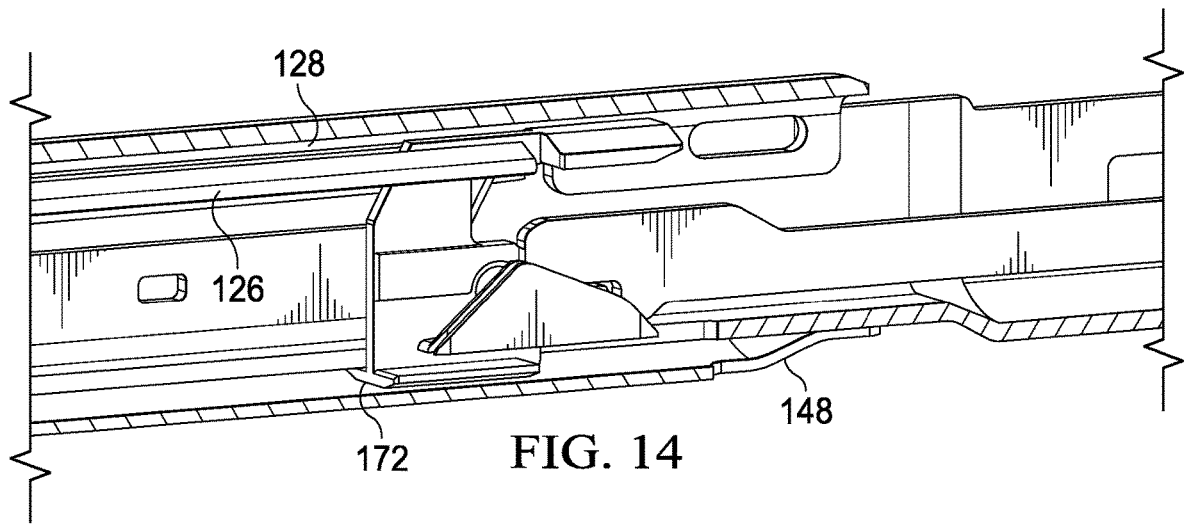
FIG. 14 depicts an implementation that prevents the transection of tissue without closure thereof with surgical staples through the use of a cantilever beam.

FIG. 14 depicts an implementation that prevents the transection of unstapled tissue. This implementation is referred to as the "cantilever beam" and includes disengaging I-beam knife 172. In FIG. 14, I-Beam knife 172 is shown as a cantilevered beam knife. In this implementation, the feature responsible for clamping down anvil plate 126 is set in front of knife 172, which transects the tissue. In this way, knife 172 cannot cut tissue without the tissue already being fastened with staples because the cantilever beam escapes anvil assembly 122 before knife 172, allowing end effector jaws 120 and 140 to be opened when knife 172 is in the proximal position. In this implementation, if tissue is present in the no tissue zone, the tissue may be stapled but will not be cut.

FIG. 15 depicts an implementation that utilizes a reversing knife approach to preventing the transection of unstapled tissue through the inclusion of a secondary thread on the primary firing screw. Formed along most of the length of firing screw 500 is a primary coarse thread 502 that provides enough travel to drive firing nut 504 from the distal end of end effector 100 to the proximal end thereof, cutting and firing staples longitudinally along the end effector. On the proximal end of firing screw 500 secondary thread segment 506 is formed having thread 506, which is finer that primary thread 502. The pitch and travel of secondary thread 506 are proportional to primary thread 502. Firing nut 504 rides along primary coarse thread 502 only and limit switch nut 508 rides along secondary fine thread 506 only. When firing screw 500 is turning, firing nut 504 and limit switch nut 508 move in the same direction but at different linear velocities and therefore travel different distances. Limit switch nut 508 will travel in between two limit switches, distal limit switch 510 and proximal limit switch 512 (see FIG. 15). Before end effector 100 is fired, firing nut 504 will be at the distal end of the end effector and limit switch nut 508 will be activating distal limit switch 510. After end effector 100 has fired, firing nut 504 will be at the proximal end of the end effector and limit switch nut 508 will be activating proximal limit switch 512.

FIG. 16 depicts an implementation that utilizes a reversing knife approach to preventing the transection of unstapled tissue through the inclusion of a secondary fine thread on an auxiliary firing screw. This implementation is similar to what shown in FIG. 15; however, auxiliary firing screw 514 obtains its rotation from firing screw 502 by way of meshed gears 516 and 518. In either implementation, primary firing screw 500 or auxiliary firing screw 514 may be any combination of left-handed or right-handed threads.

Figure 17:
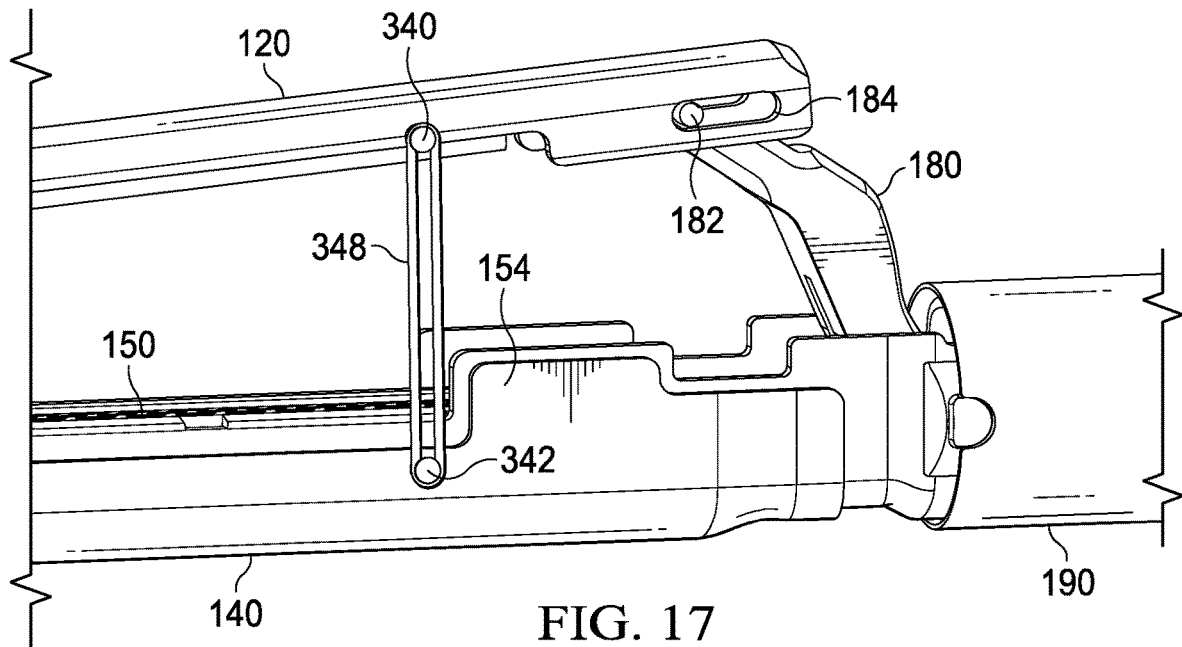
FIG. 17 depicts the stapler of FIG. 1A, where the jaws of the stapler are shown in an open position and where a tissue-blocking elastomeric band has been mounted on an attachment screw on the upper jaw and an attachment screw on the lower jaw.
Figure 18:
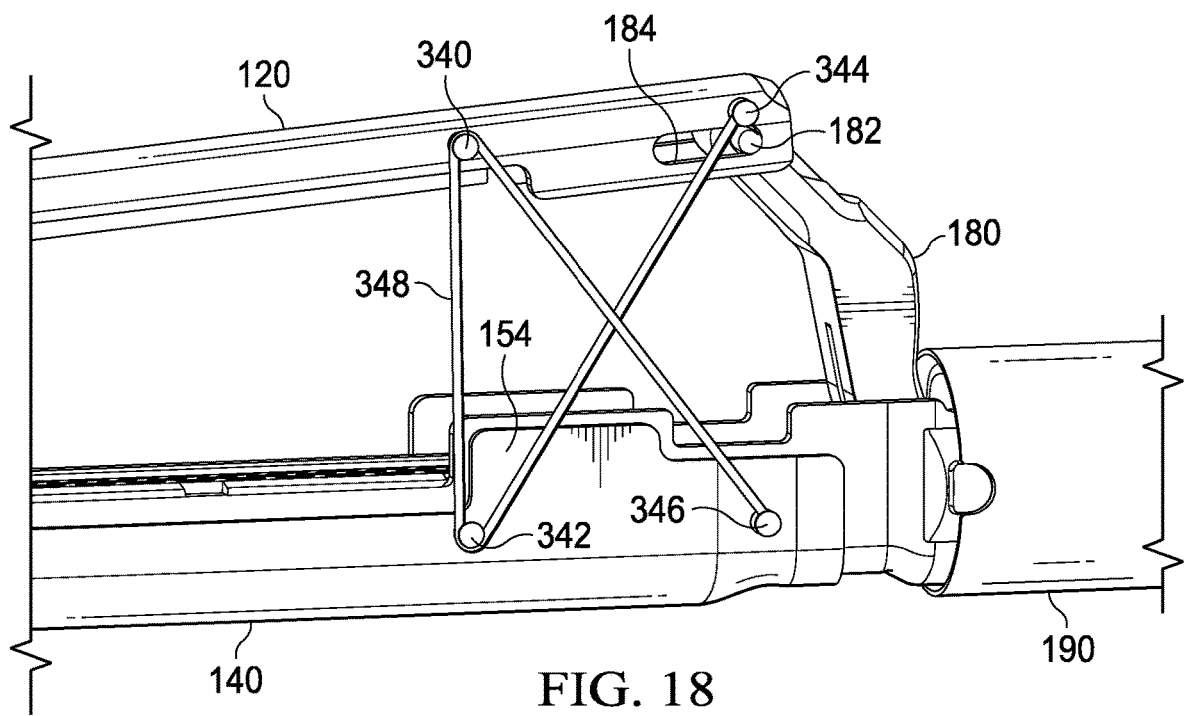
FIG. 18 depicts the stapler of FIG. 1A, wherein the jaws of the stapler are shown in an open position and wherein a tissue-blocking elastomeric band has been mounted on two attachment screws on the upper jaw and two attachment screws on the lower jaw in a crossed configuration.
Figure 19:
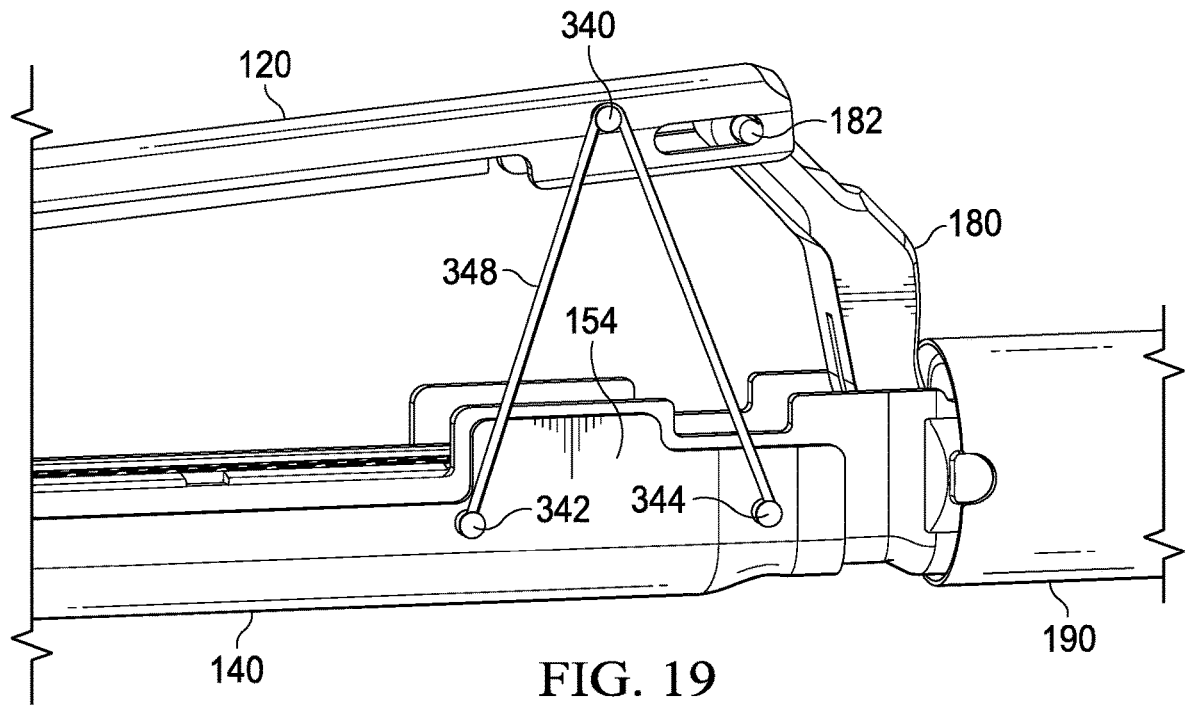
FIG. 19 depicts the stapler of FIG. 1A, wherein the jaws of the stapler are shown in an open position and wherein a tissue-blocking elastomeric band has been mounted an attachment screw on the upper jaw and two attachment screws on the lower jaw in a triangular configuration.

FIG. 17 depicts an implementation of end effector 100, wherein the jaws of end effector 100 are shown in an open position and where tissue-blocking elastomeric band 348 has been mounted on attachment screw 340 on upper jaw 120 and attachment screw 342 on lower jaw 140. FIG. 18 depicts end effector 100, where the jaws of end effector 100 are shown in an open position and where tissue-blocking elastomeric band 348 has been mounted on attachment screws 340 and 344 on upper jaw 120 and attachment screws 342 and 346 on lower jaw 140 in a crossed configuration. FIG. 19 depicts end effector 100, wherein the jaws of end effector 100 are shown in an open position and where tissue-blocking elastomeric band 348 has been mounted on attachment screw 340 on upper jaw 120 and attachment screws 342 and 344 on lower jaw 140 in a triangular configuration. Elastic band 348 may be silicone, urethane, or similar material, and may be a full loop or an elastic string. In alternate implementations, the attachments screws are replaced with rivets, glued posts, welded posts, or stamped or molded features formed on upper and lower jaws 120 and 140.

Figure 20:
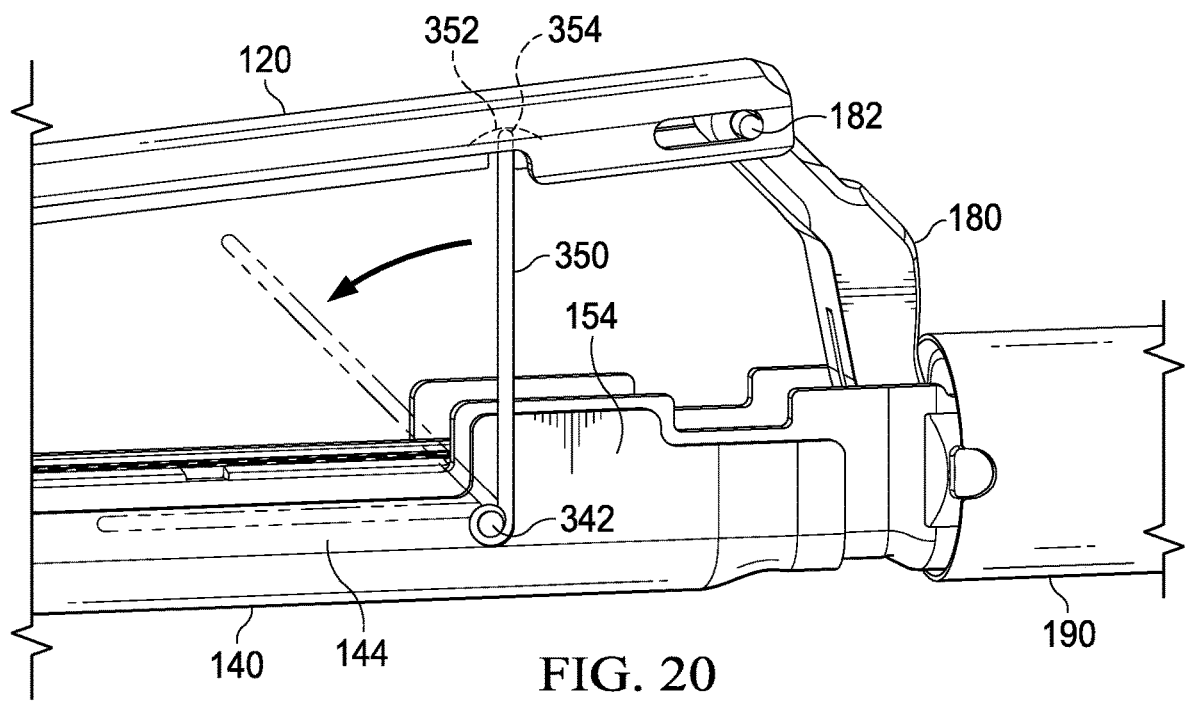
FIG. 20 depicts the stapler of FIG. 1A, wherein the jaws of the stapler are shown in an open position and wherein a tissue-blocking rotating post has been positioned between the upper and lower jaws of the stapler.

FIG. 20 depicts an implementation of end effector 100, where the jaws of end effector 100 are shown in an open position and wherein tissue-blocking rotating post 350 has been positioned between upper and lower jaws 120 and 140 of end effector 100. In the implementation shown in FIG. 20, attachment point 342 includes a torsional spring that biases post 350 in a vertical position. When jaws 120 and 140 are open, the torsional spring rotates post 350 upward, perpendicular to cartridge frame 144. When jaws 120 and 140 close, a moment is applied to post attachment point 342 by way of anvil frame 124 on the end of post 350 that counteracts the force on the torsional spring and rotates post 350 counterclockwise or clockwise until post 350 is parallel, or nearly parallel, to cartridge frame 144. FIG. 20 also depicts an alternate configuration, wherein the end of post 350 opposite attachment point 342 is constrained by cam profile 352 on anvil frame 124, and wherein the end of post 350 opposite attachment point 342 acts as cam follower 354. As jaws 120 and 140 open, cam profile 352 forces cam follower 354 into a vertical position, perpendicular to cartridge frame 144. As jaws 120 and 140 close, cam profile 352 forces cam follower 354 into a horizontal position, parallel, or nearly parallel, to cartridge frame 144. This implementation may include any combination of a torsional spring, and cam profile and cam follower.

Figure 21:
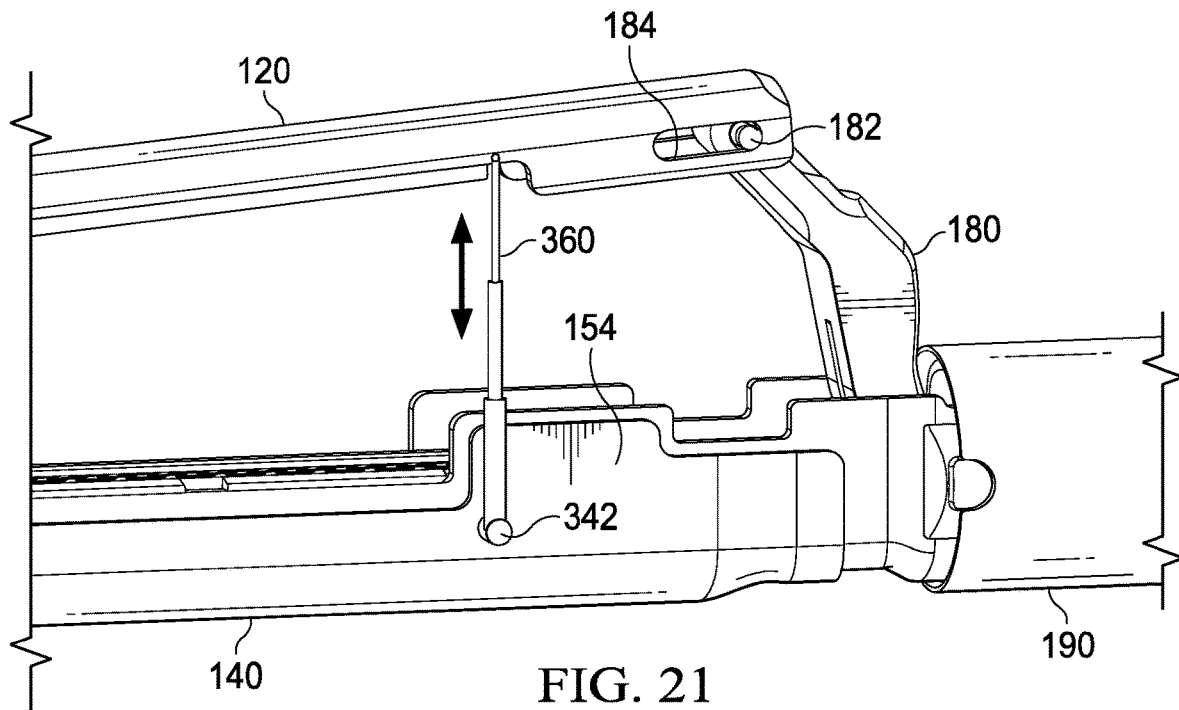
FIG. 21 depicts the stapler of FIG. 1A, wherein the jaws of the stapler are shown in an open position and where a tissue-blocking telescoping post has been positioned between the upper and lower jaws of the stapler.

FIG. 21 depicts an implementation of end effector 100, wherein the jaws of end effector 100 are shown in an open position and wherein tissue-blocking telescoping post 360 has been positioned between upper and lower jaws 120 and 140 of end effector 100. In the implementation shown in FIG. 21, post 360 does not rotate but telescopically translates in a vertical manner. Telescoping post 360 may be biased upward using a compression spring that is compressed when jaws 120 and 140 close. When jaws 120 and 140 open, the compression spring forces the inner telescopic members of post 360 upward. A structure such as, for example, a ball and socket joint, may be included on anvil frame 124 for constraining the lateral movement of telescoping post 360 and providing a surface for compressing post 360. This structure or feature may be attached to anvil frame 124 using screws, rivets, glue, welding, or by using features stamped or molded into anvil frame 124.

Figure 22:
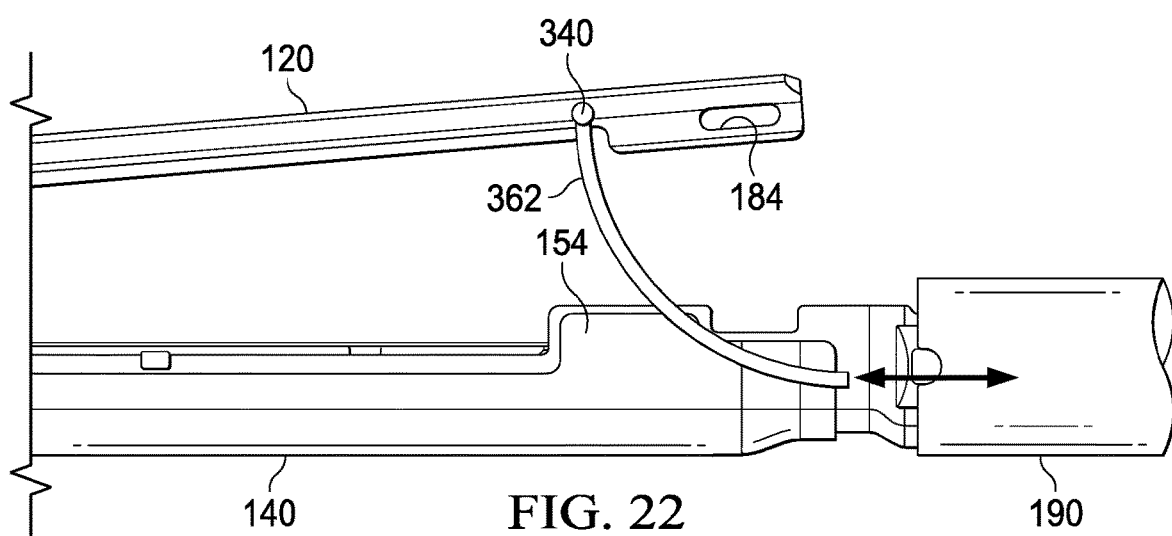
FIG. 22 depicts the stapler of FIG. 1A, wherein the jaws of the stapler are shown in an open position and where a tissue-blocking curved linkage has been positioned between the upper and lower jaws of the stapler.

FIG. 22 depicts an implementation of end effector 100, where the jaws of end effector 100 are shown in an open position and wherein tissue-blocking curved linkage 362 has been positioned between upper and lower jaws 120 and 140 of end effector 100. In the implementation shown in FIG. 22, curved linkage 362 is used to clamp upper jaw 120 to lower jaw 140. Curved linkage 362 is pinned in anvil frame 124 wherein it rotates freely. Curved linkage 362 pivots or slides near cartridge 150 as it is pushed or pulled from inside support tube 190 to open or close jaws 120 and 140. Curved linkage 362 is present inside the no tissue zone, thereby shielding tissue from entering it, and is bowed to allow adjacent tissue in jaws 120 and 140 to be pushed out of the no tissue zone.

Figure 23:
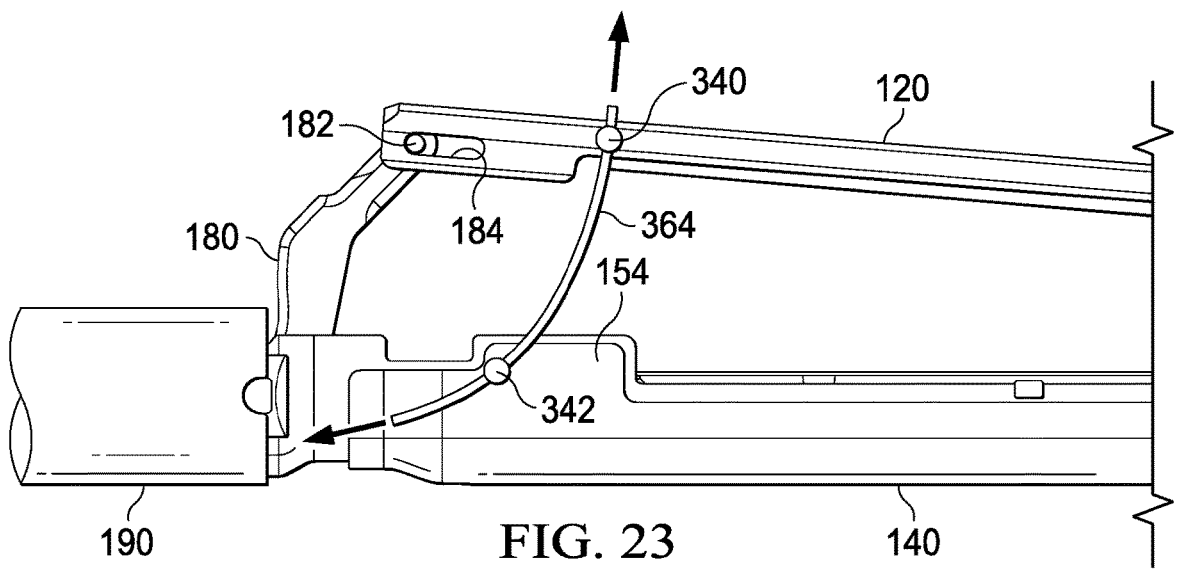
FIG. 23 depicts the stapler of FIG. 1A, wherein the jaws of the stapler are shown in an open position and where a tissue-blocking passive curved linkage has been positioned between the upper and lower jaws of the stapler.

FIG. 23 depicts an implementation of end effector 100, where the jaws of end effector 100 are shown in an open position and wherein tissue-blocking passive curved linkage 362 has been positioned between upper and lower jaws 120 and 140 of end effector 100. In the implementation shown in FIG. 23, curved linkage 364 includes a passive band that cooperates with a separate linkage. The band is pinned on upper jaw 120 at 340 and pivots in lower jaw 140 at pivot point 342. The passive band does not mechanically clamp jaws 120 and 140 together but shields the no tissue zone. The passive band is pulled underneath the separate link when jaws 120 and 140 are closed. When jaws 120 and 140 are opened, the passive band is bowed and present in the no tissue zone.

Figure 24:
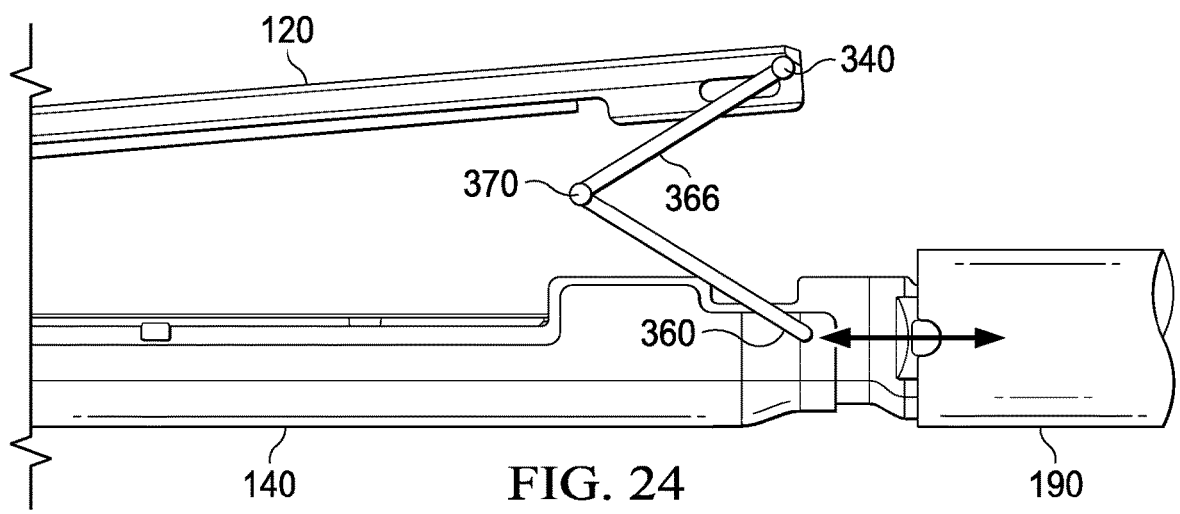
FIG. 24 depicts the stapler of FIG. 1A, wherein the jaws of the stapler are shown in an open position and where a tissue-blocking pivoting double linkage has been positioned between the upper and lower jaws of the stapler.

FIG. 24 depicts an implementation of end effector 100, where the jaws of end effector 100 are shown in an open position and where a tissue-blocking pivoting double linkage 365 has been positioned between upper and lower jaws 120 and 140 of end effector 100. Double linkage 365, which has an additional degree of freedom compared to other disclosed implementations, includes first link 366 connected to second link 370 at pivot point 370. When jaws 120 and 140 are closing, pivot point 370 pushes tissue out of the no tissue zone, if present, and double linkage 365 then folds into cartridge frame 144. When jaws 120 and 140 are opening, the double linkage unfolds and becomes a rigid member that shields the no tissue zone. Double linkage 365 is connected to anvil frame 124 in a hinged manner at attachment point 340.

Figure 25:
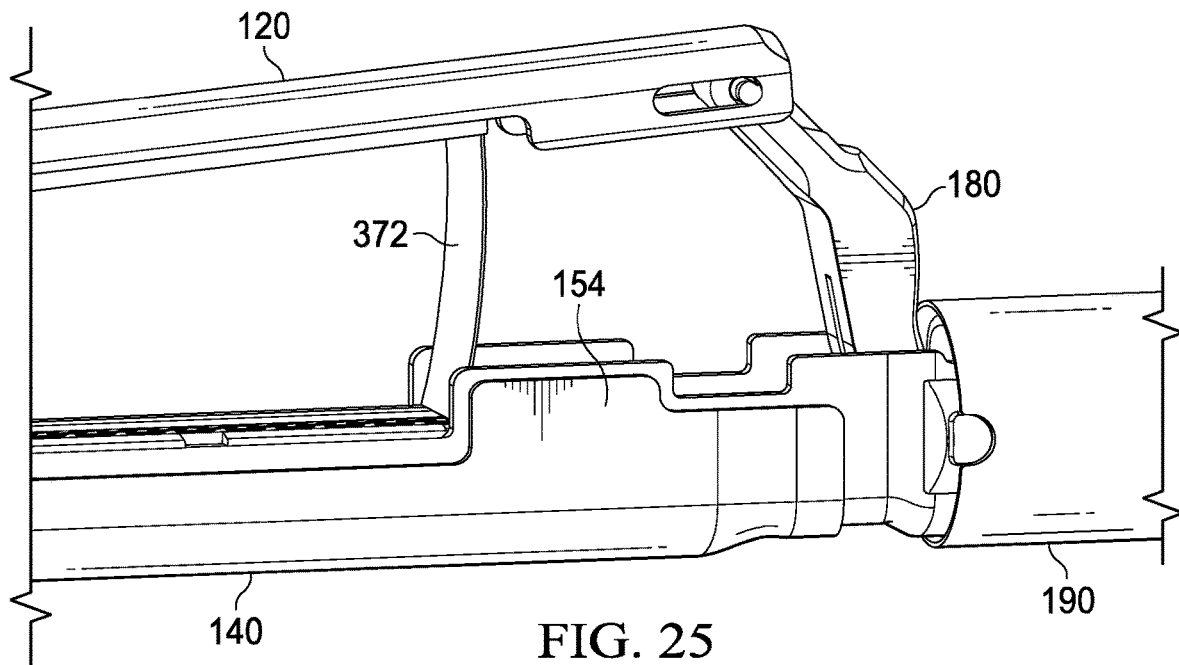
FIG. 25 depicts the stapler of FIG. 1A, wherein the jaws of the stapler are shown in an open position and where a tissue-blocking sacrificial cut band has been positioned between the upper and lower jaws of the stapler.

FIG. 25 depicts an implementation of end effector 100, wherein the jaws of end effector 100 are shown in an open position and where a tissue-blocking sacrificial cut band 372 has been positioned between upper and lower jaws 120 and 140 of end effector 100. In the implementation shown in FIG. 25, sacrificial cut band 372 occupies the entire distance between upper and lower jaws 120 and 140 and the entire width of both cartridge frame 144 and anvil frame 124. Sacrificial cut band 372 is cut or destroyed when I-Beam knife 172 fires through the band at the end of the firing stroke of knife 172. The sacrificial band is typically made from a soft material, such as silicone, urethane, or any other suitable material, so that knife 172 can effectively fire through the band. The band shields tissue from the no tissue zone while also allowing the jaws of the end effector device to close.

Figure 26:
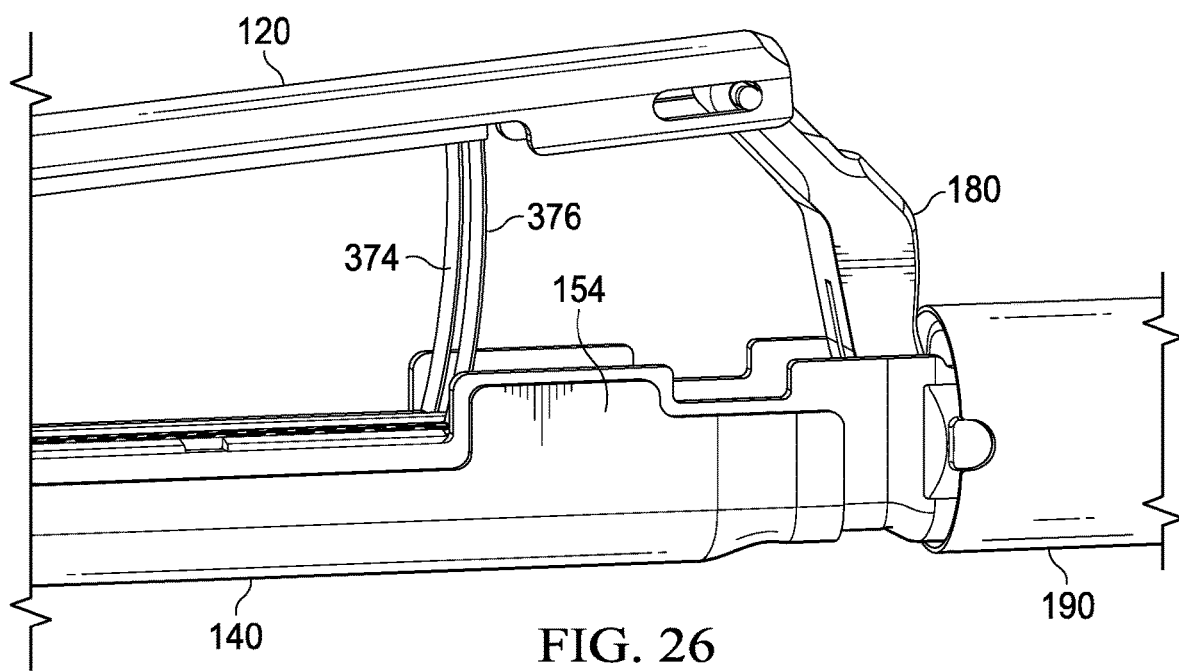
FIG. 26 depicts the stapler of FIG. 1A, wherein the jaws of the stapler are shown in an open position and wherein a tissue-blocking split band has been positioned between the upper and lower jaws of the stapler.

FIG. 26 depicts an implementation of end effector 100, where the jaws of end effector 100 are shown in an open position and wherein a tissue-blocking split band 373 has been positioned between upper and lower jaws 120 and 140 of end effector 100. In the implementation shown in FIG. 26, split band 373 includes first band portion 374 and separate second band portion 376 for allowing I-Beam knife 172 to pass through the separate band portions when fired. Split band 373 may be attached to cartridge frame 144 or cartridge 150 on lower jaw 140 and to anvil frame 124 on upper jaw 120. Split band 373 shields tissue from the no tissue zone while also allowing the jaws of the end effector device to close.

Figure 27:
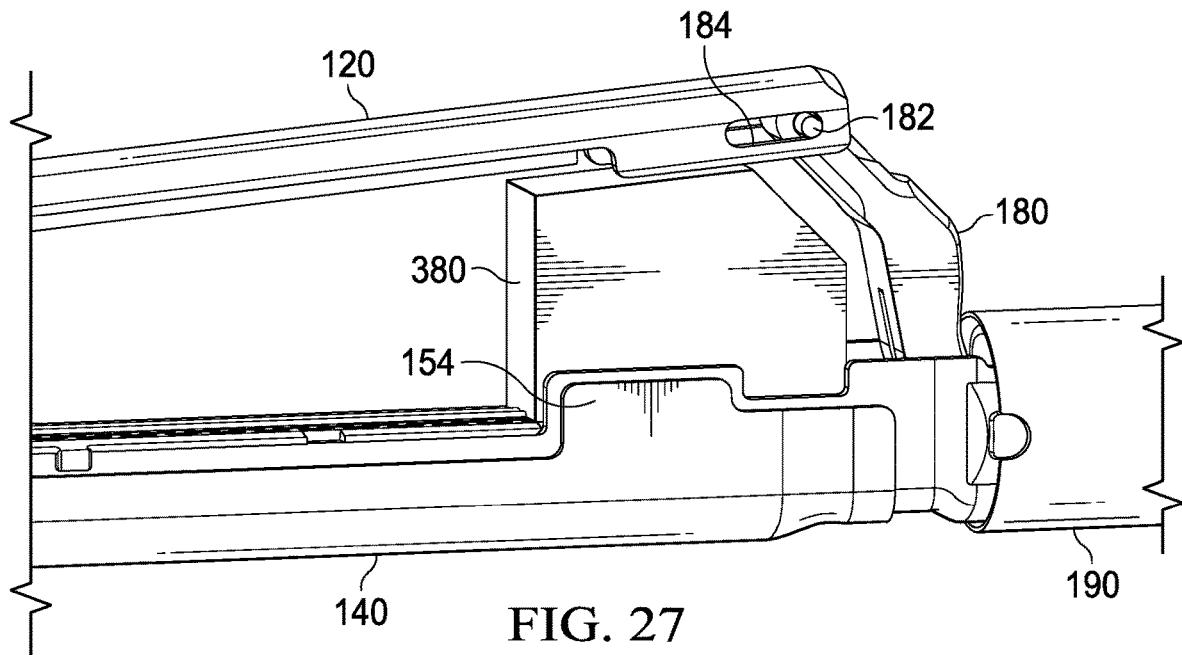
FIG. 27 depicts the stapler of FIG. 1A, wherein the jaws of the stapler are shown in an open position and wherein a tissue-blocking compliant sacrificial foam block has been positioned between the upper and lower jaws of the stapler.
Figure 28:
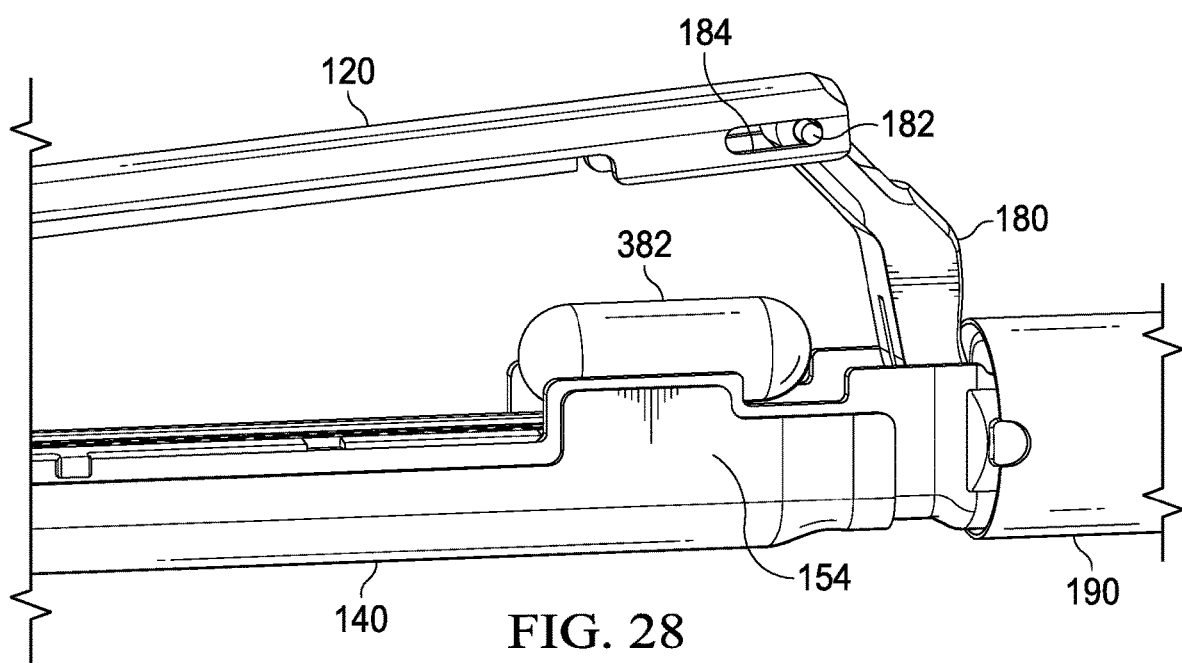
FIG. 28 depicts the stapler of FIG. 1A, wherein the jaws of the stapler are shown in an open position and wherein a tissue-blocking compliant sacrificial balloon has been positioned between the upper and lower jaws of the stapler.

FIG. 27 depicts an implementation of end effector 100, wherein the jaws of end effector 100 are shown in an open position and where tissue-blocking compliant sacrificial foam block 380 has been positioned between upper and lower jaws 120 and 140 of end effector 100. FIG. 28 depicts an implementation of end effector 100, where the jaws of end effector 100 are shown in an open position and wherein tissue-blocking compliant sacrificial balloon 382 has been positioned between upper and lower jaws 120 and 140 of end effector 100. Both compliant sacrificial foam block 380 and compliant sacrificial balloon 382 can permit I-beam knife 172 to pass through the area of end effector 100 occupied by these elements or features. Compliant sacrificial foam block 380 may be attached to anvil frame 124, cartridge frame 144, cartridge 150, or may be simply constrained by the components surrounding the no tissue zone. The block is compliant, in an example, and may be fabricated from an open cell foam or closed cell foam, and allows upper and lower jaws 120 and 140 to clamp together. The block can include a specific density that allows I-Beam knife 172 to fire through it when compressed. The compliant block may be sacrificial and may be destroyed from the firing sequence of end effector 100. Compliant sacrificial balloon 382 can be a gas filled compliant balloon, rather than a block, that allows upper and lower jaws 120 and 140 to clamp together without bursting and may be destroyed from the firing sequence of end effector 100. The compliant balloon may be attached to anvil frame 124, cartridge frame 144, cartridge 150, or may be simply constrained by the components surrounding the no tissue zone.

Figure 29:
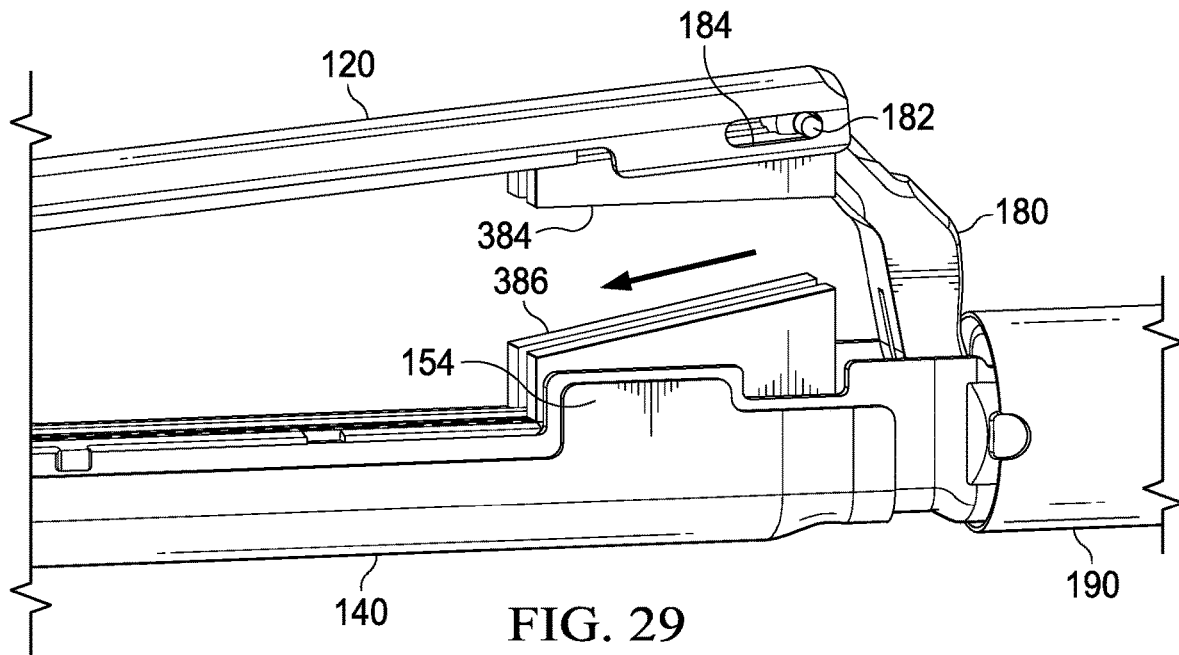
FIG. 29 depicts the stapler of FIG. 1A, wherein the jaws of the stapler are shown in an open position and wherein a zero-clearance block has been positioned between the upper and lower jaws of the stapler.

FIG. 29 depicts an implementation of end effector 100, wherein the jaws of end effector 100 are shown in an open position and wherein tissue-blocking zero clearance block 383 having top portion 384 and bottom portion 386 has been positioned between upper and lower jaws 120 and 140 of end effector 100. In the implementation shown in FIG. 29, zero clearance block 383 is neither compliant nor sacrificial, but rather is a rigid tapered block attached to both upper and lower jaws 120 and 140 that pushes clamped tissue out of the no tissue zone. Both top portion 384 and bottom portion 386 can include a centrally placed channel or gap that permits I-beam knife 172 to travel through each portion. Rigid tapered block 383 may be a structure integrated into anvil frame 124 and cartridge frame 144 (or cartridge 150) or it may be a separate component fabricated from rigid plastic such as nylon or from metal such as stainless steel. If the rigid tapered block is a separate component, it may be attached to upper and lower jaws 120 and 140 by gluing, welding, snap features, or with hardware such as bolts or screws. The rigid block may produce zero clearance in the no tissue zone when the jaws of end effector 100 are closed.

Figure 30:
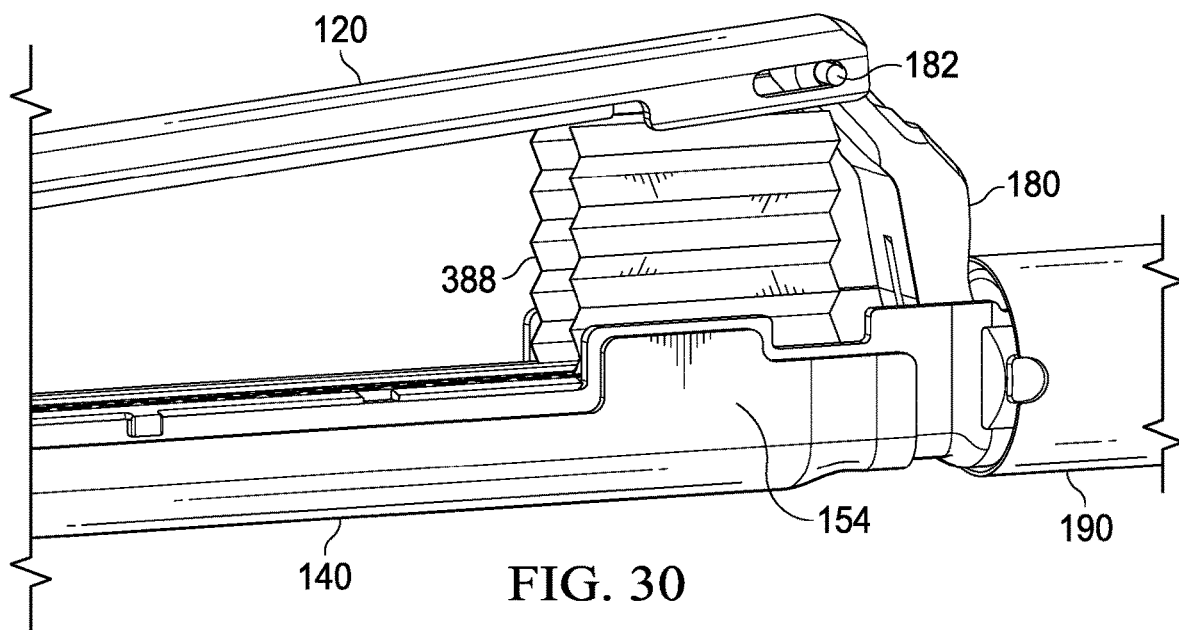
FIG. 30 depicts the stapler of FIG. 1A, wherein the jaws of the stapler are shown in an open position and wherein an accordion-like tissue blocking device has been positioned between the upper and lower jaws of the stapler.
Figure 31:
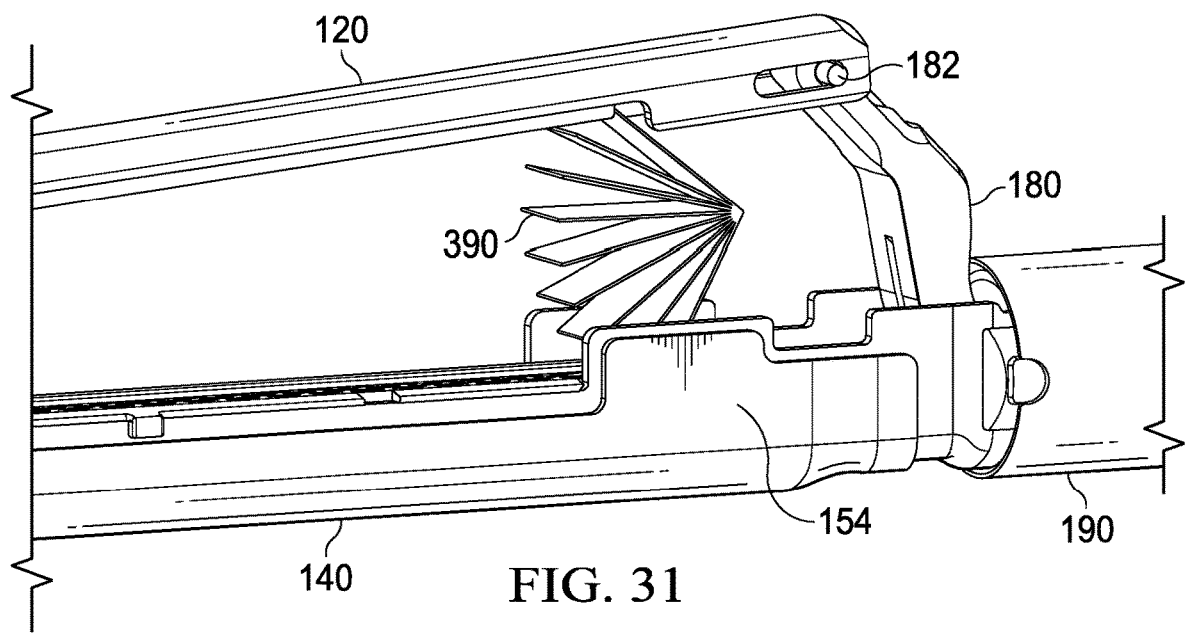
FIG. 31 depicts the stapler of FIG. 1A, wherein the jaws of the stapler are shown in an open position and wherein an alternate accordion-like tissue blocking device has been positioned between the upper and lower jaws of the stapler.

FIGS. 30 and 31 depict alternate devices and methods of shielding the no tissue zone by using an accordion-like shield that can "fan out" when the jaws of the end effector are open and "fold in" when the jaws of the end effector are closed. Example devices can be attached to upper and lower jaws 120 and 140 to give the shield two or more anchor points when pulled apart. These accordion-like devices may be fabricated from a rigid or flexible metal or plastic or any other suitable material. FIG. 30 depicts an implementation of end effector 100, where the jaws of end effector 100 are shown in an open position and where accordion shield 388 has been positioned between upper and lower jaws 120 and 140 of end effector 100. Accordion shield 388 extends along each side of the no tissue zone and maintains its overall footprint when extended. In this implementation, I-Beam knife 172 can travel in-between the two sides of the accordion shield. FIG. 31 depicts an implementation of end effector 100, where the jaws of end effector 100 are shown in an open position and where fan shield 390 has been positioned between upper and lower jaws 120 and 140 of end effector 100. In the implementation shown in FIG. 31, fan shield 390 fans out distally when extended and extends in a semi-circular pattern from a central axis inside the no tissue zone. Fan shield 390 may be sacrificial, destroyed by knife 172 during the firing sequence of end effector 100, or it may be split into two separate fans to allow knife 172 to pass through the no tissue zone.

Figure 32:
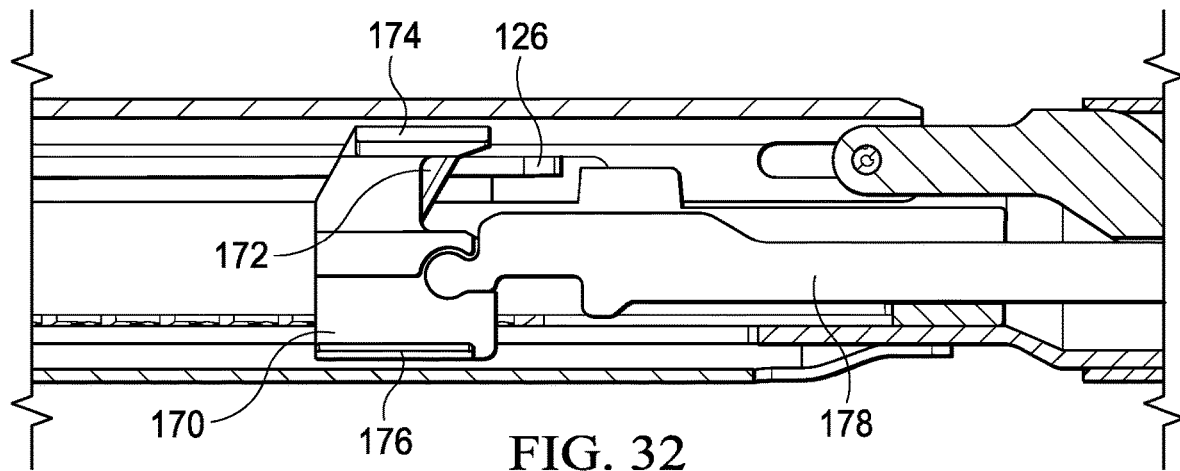
FIG. 32 depicts an implementation that utilizes disengaging I-beam knife approach (normal orientation) to prevent the transection of tissue without the closure thereof with surgical staples.
Figure 33:
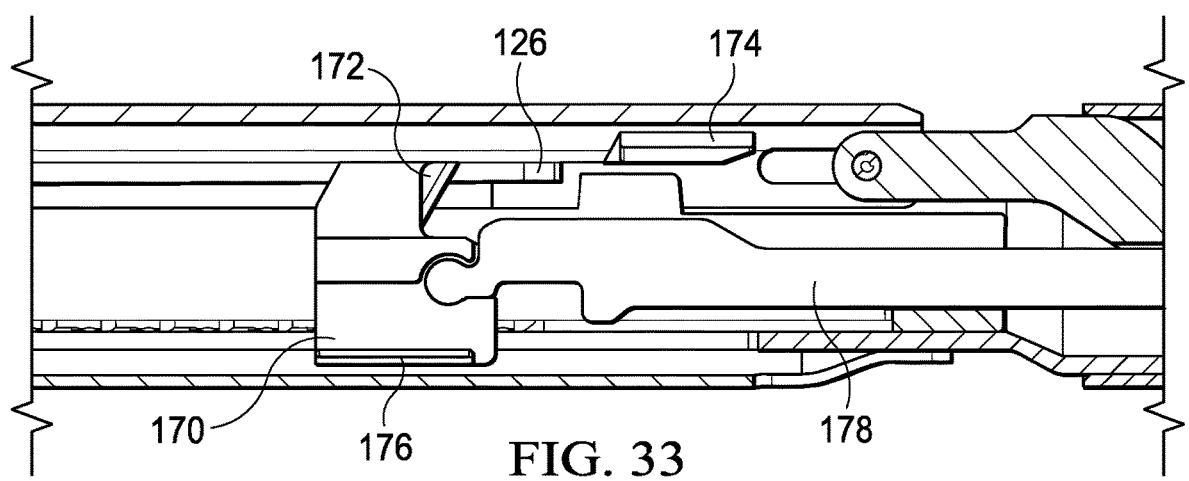
FIG. 33 depicts an implementation that utilizes a disengaging I-beam knife approach, shown in a disengaged orientation, to prevent the transection of tissue without the closure thereof with surgical staples.

FIG. 32 depicts an implementation that utilizes a disengaging I-beam knife approach (normal orientation) to prevent the transection of unstapled tissue and FIG. 33 depicts an implementation that utilizes a disengaging I-beam knife approach (disengage orientation) to prevent the transection of unstapled tissue. In the implementations shown in FIGS. 32 and 33, I-beam top shelf 174 can be disengaged from anvil plate 126 at proximal tissue stop 154. In these implementations, knife 172 stops at proximal tissue stop 154 or in front of the no tissue zone, but I-beam top shelf 174 may continue on a separate linear travel mechanism until it clears anvil plate 126 as shown in FIG. 33. Alternately, I-beam top shelf 174 may become free from I-Beam 170 by means of a mechanical fuse or the like, thereby allowing upper jaw 120 to open relative to lower jaw 140. In a similar fashion, I-beam bottom shelf 176 may be disengaged. I-beam top shelf 174 may be disengaged from anvil frame 124 and I-beam bottom shelf 176 may become disengaged from cartridge frame 144 by a trap door or a moving door mechanism, allowing the end effector jaws to open without being constrained by the top and/or bottom shelf.

Figure 34:
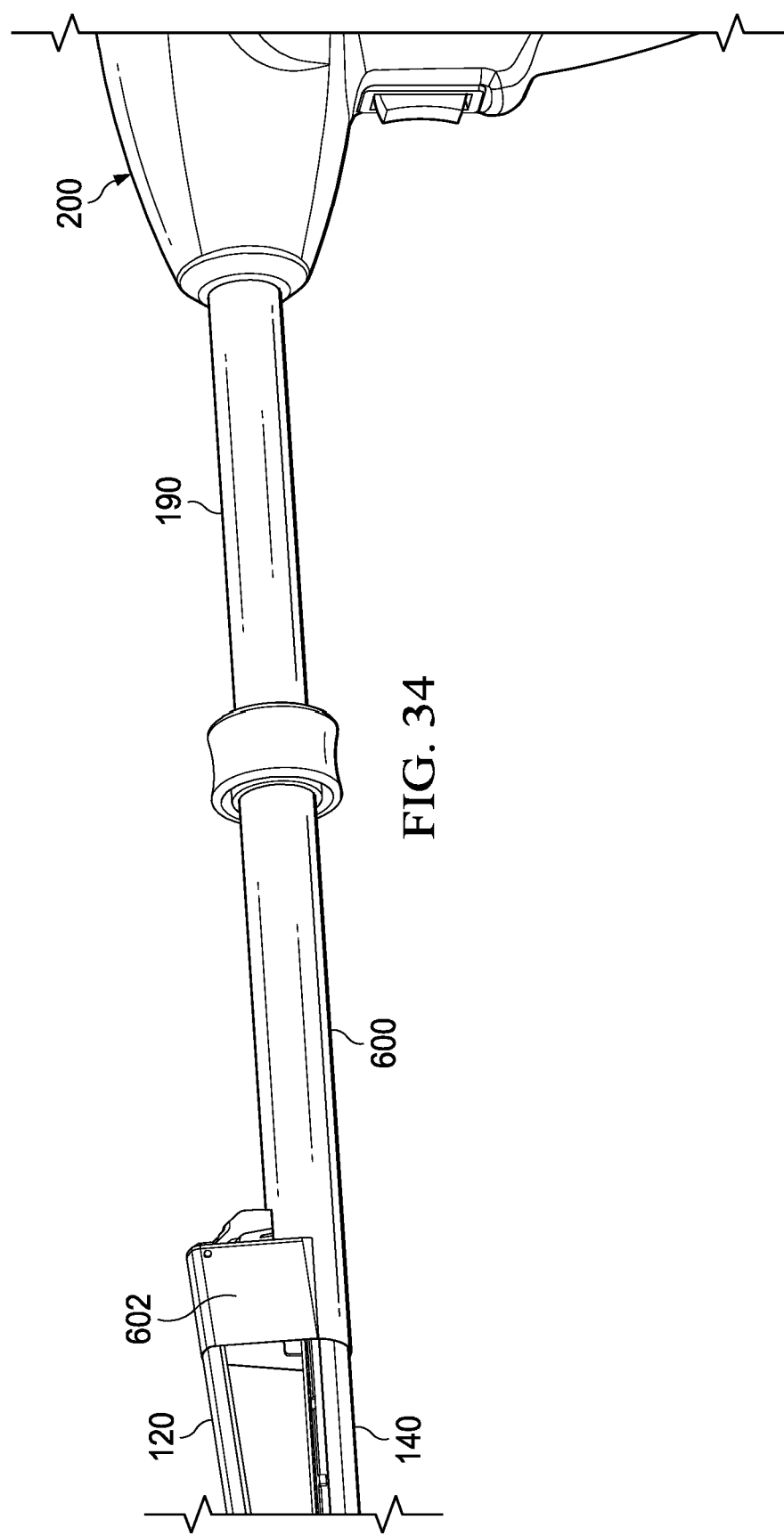
FIG. 34 depicts an implementation that utilizes an external device or introducer sheath to shield a no tissue zone.

FIG. 34 depicts an implementation that utilizes an external device referred to as an introducer sheath to shield the no tissue zone. In the implementation shown in FIG. 34, introducer sheath 600 is not fixed to end effector 100, but slides longitudinally along the stapling instrument and may be concentric to the end effector 100. Introducer sheath 600 may cooperate with a trocar, a shielding sheath, or another device. Shielding sheath 602 may be flexible in the no tissue zone location, allowing the end effector jaws to open, close, and fit through a trocar while still shielding the no tissue zone.

All literature and similar material cited in this application, including, but not limited to, patents, patent applications, articles, books, treatises, and web pages, regardless of the format of such literature and similar materials, are expressly incorporated by reference in their entirety. Should one or more of the incorporated references and similar materials differs from or contradicts this application, including but not limited to defined terms, term usage, described techniques, or the like, this application controls.

As previously stated and as used herein, the singular forms "a," "an," and "the" refer to both the singular as well as plural, unless the context clearly indicates otherwise. The term "comprising" as used herein is synonymous with "including," "containing," or "characterized by," and is inclusive or open-ended and does not exclude additional, unrecited elements or method steps. Although many methods and materials similar or equivalent to those described herein can be used, particular suitable methods and materials are described herein. Unless context indicates otherwise, the recitations of numerical ranges by endpoints include all numbers subsumed within that range. Furthermore, references to "one implementation" are not intended to be interpreted as excluding the existence of additional implementations that also incorporate the recited features. Moreover, unless explicitly stated to the contrary, implementations "comprising" or "having" an element or a plurality of elements having a particular property may include additional elements whether or not they have that property.

The terms "substantially" and "about" used throughout this specification are used to describe and account for small fluctuations, such as due to variations in processing. For example, these terms can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%, and/or 0%.

Underlined and/or italicized headings and subheadings are used for convenience only, do not limit the disclosed subject matter, and are not referred to in connection with the interpretation of the description of the disclosed subject matter. All structural and functional equivalents to the elements of the various implementations described throughout this disclosure that are known or later come to be known to those of ordinary skill in the art are expressly incorporated herein by reference and intended to be encompassed by the disclosed subject matter. Moreover, nothing disclosed herein is intended to be dedicated to the public regardless of whether such disclosure is explicitly recited in the above description.

There may be many alternate ways to implement the disclosed inventive subject matter. Various functions and elements described herein may be partitioned differently from those shown without departing from the scope of the disclosed inventive subject matter. Generic principles defined herein may be applied to other implementations. Different numbers of a given module or unit may be employed, a different type or types of a given module or unit may be employed, a given module or unit may be added, or a given module or unit may be omitted.

It should be appreciated that all combinations of the foregoing concepts and additional concepts discussed in greater detail herein (provided such concepts are not mutually inconsistent) are contemplated as being part of the disclosed inventive subject matter. In particular, all combinations of claimed subject matter appearing at the end of this disclosure are contemplated as being part of the inventive subject matter disclosed herein. While the disclosed inventive subject matter has been illustrated by the description of example implementations, and while the example implementations have been described in certain detail, there is no intention to restrict or in any way limit the scope of the appended claims to such detail. Additional advantages and modifications will readily appear to those skilled in the art. Therefore, the disclosed inventive subject matter in its broader aspects is not limited to any of the specific details, representative devices and methods, and/or illustrative examples shown and described. Accordingly, departures may be made from such details without departing from the spirit or scope of the general inventive concept.

What is claimed is:

1. A surgical instrument, comprising:
an end effector, wherein the end effector includes:
(i) an upper jaw the upper jaw including a proximal end and a distal end;
(ii) a lower jaw, the lower jaw including a proximal end and a distal end, wherein the distal end of the upper jaw is connected to the distal end of the lower jaw, and wherein the proximal end of the upper jaw is connected to the proximal end of the lower jaw;
(iii) a knife assembly comprising a knife, a beam, and a firing nut, wherein the beam is coupled to the firing nut;
(iv) a firing lead screw having a threaded portion, wherein a distal end of the firing lead screw is coupled to a bushing, wherein rotation of the firing lead screw in a first direction proximally drives the firing nut along the threaded portion and rotation of the firing lead screw in a second direction distally drives the firing nut along the threaded portion, and wherein the firing lead screw has an unthreaded portion extending between the bushing and the threaded portion; and
(v) a firing screw compression spring extending along the firing lead screw, wherein the firing screw compression spring is positioned between the bushing and the firing nut.

2. The surgical instrument of claim 1, wherein the compression spring has a distal end and a proximal end, and wherein the distal end is coupled to the bushing.

3. The surgical instrument of claim 1, wherein the compression spring extends along at least a portion of the unthreaded portion.

4. The surgical instrument of claim 3, wherein the compression spring applies a load proximally on the firing nut when the firing nut is driven from the threaded portion at least partially onto the unthreaded portion.

5. The surgical instrument of claim 1, wherein the compression spring has a distal end and a proximal end, and wherein the proximal end of the compression spring is coupled to the firing nut.

6. The surgical instrument of claim 5, wherein rotation of the firing lead screw in a first direction proximally translates the compression spring along the firing lead screw and rotation of the firing lead screw in a second direction distally translates the compression spring along the firing lead screw.

7. The surgical instrument of claim 6, further comprising a nut plate, wherein the nut plate is positioned along the firing lead screw between the firing nut and the bushing, and wherein the distal end of the compression spring is coupled to the nut plate.

8. The surgical instrument of claim 7, wherein the nut plate is unthreaded, wherein rotation of the firing lead screw in a first direction proximally translates the nut plate, compression spring, and firing nut along the firing lead screw and rotation of the firing lead screw in a second direction distally translates the nut plate, compression spring, and firing nut along the firing lead screw.

9. A surgical instrument, comprising:
an end effector, wherein the end effector includes:
(i) an upper jaw the upper jaw including a proximal end and a distal end;
(ii) a lower jaw, the lower jaw including a proximal end and a distal end, wherein the distal end of the upper jaw is connected to the distal end of the lower jaw, and wherein the proximal end of the upper jaw is connected to the proximal end of the lower jaw;
(iii) a knife assembly comprising a knife, a beam, and a firing nut, wherein the beam is coupled to the firing nut, wherein the firing nut has a proximal side and a distal side;
(iv) a firing lead screw having a distal end and a proximal end, wherein rotation of the firing lead screw in a first direction proximally drives the firing nut along the firing lead screw and rotation of the firing lead screw in a second direction distally drives the firing nut along the firing lead screw; and
(v) a firing screw compression spring extending along the firing lead screw, wherein the firing screw compression spring is positioned between the firing nut and the distal end of the firing lead screw, wherein rotation of the firing lead screw in a first direction proximally translates the compression spring along the firing lead screw and rotation of the firing lead screw in a second direction distally translates the compression spring along the firing lead screw.

10. The surgical instrument of claim 9, further comprising a bushing, wherein the distal end of the firing lead screw is coupled to the bushing, wherein the compression spring has a distal end and a proximal end, wherein the distal end is coupled to the bushing.

11. The surgical instrument of claim 10, wherein a portion of the firing lead screw proximate to the distal end is an unthreaded portion.

12. The surgical instrument of claim 11, wherein the compression spring extends along at least a portion of the unthreaded portion.

13. The surgical instrument of claim 11, wherein the compression spring applies a load proximally on the firing nut when the firing nut is driven onto the unthreaded portion.

14. The surgical instrument of claim 9, wherein the compression spring has a distal end and a proximal end, wherein the proximal end of the compression spring is coupled to the firing nut.

15. The surgical instrument of claim 9, further comprising a nut plate, wherein the nut plate is positioned along the firing lead screw, and wherein the distal end of the compression spring is coupled to the nut plate.

16. The surgical instrument of claim 15, wherein the nut plate is unthreaded, wherein rotation of the firing lead screw in a first direction proximally translates the nut plate, compression spring, and firing nut along the firing lead screw and rotation of the firing lead screw in a second direction distally translates the nut plate, compression spring, and firing nut along the firing lead screw.

17. The surgical instrument of claim 16, further comprising a bushing, wherein the distal end of the firing lead screw is coupled to the bushing, wherein rotation of the firing lead screw in the second direction distally translates the nut plate along the firing lead screw to bring the nut plate in contact with the bushing and compress the compression spring.

18. A surgical instrument, comprising:
an end effector, wherein the end effector includes:
(i) an upper jaw the upper jaw including a proximal end and a distal end;
(ii) a lower jaw, the lower jaw including a proximal end and a distal end, wherein the distal end of the upper jaw is connected to the distal end of the lower jaw, and wherein the proximal end of the upper jaw is connected to the proximal end of the lower jaw;
(iii) a knife assembly comprising a knife, a beam, and a firing nut, wherein the beam is coupled to the firing nut;
(iv) a firing lead screw having a threaded portion and unthreaded portion, wherein rotation of the firing lead screw in a first direction proximally drives the firing nut along the threaded portion and rotation of the firing lead screw in a second direction distally drives the firing nut along the threaded portion towards the unthreaded portion; and
(v) a firing screw compression spring extending along the firing lead screw, wherein the compression spring applies a load proximally on the firing nut when the firing nut is driven onto the unthreaded portion.

* * * * *